(12) United States Patent
Demarest et al.

(10) Patent No.: US 7,503,675 B2
(45) Date of Patent: Mar. 17, 2009

(54) COMBINATION LIGHT DEVICE WITH INSECT CONTROL INGREDIENT EMISSION

(75) Inventors: Scott W. Demarest, Caledonia, WI (US); Simon M. Conway, Burlington, WI (US); Scott D. Walter, Twin Lakes, WI (US); Matthew Abbondanzio, Racine, WI (US); Darren K. Robling, Racine, WI (US); Gopal P. Ananth, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 78 days.

(21) Appl. No.: 11/620,966

(22) Filed: Jan. 8, 2007

(65) Prior Publication Data

US 2007/0133206 A1    Jun. 14, 2007

Related U.S. Application Data

(63) Continuation-in-part of application No. 11/426,055, filed on Jun. 23, 2006, now Pat. No. 7,318,659, which is a continuation-in-part of application No. 11/069,964, filed on Mar. 3, 2005, now Pat. No. 7,246,919, application No. 11/620,966, which is a continuation-in-part of application No. 10/561,822, filed on Apr. 25, 2006.

(60) Provisional application No. 60/549,154, filed on Mar. 3, 2004.

(51) Int. Cl.
    *F21V 33/00* (2006.01)

(52) U.S. Cl. ............... 362/253; 362/441; 392/393
(58) Field of Classification Search ............... 362/253, 362/643, 441; 392/393, 394
    See application file for complete search history.

(56) References Cited

U.S. PATENT DOCUMENTS 1,535,486 A    4/1925    Lundy (Continued)

FOREIGN PATENT DOCUMENTS

FR    2628244    9/1989

(Continued)

OTHER PUBLICATIONS

International Searching Authority, "International Search Report and Written Opinion", May 26, 2008, 11 Sheets.

*Primary Examiner*—Ali Alavi
*Assistant Examiner*—Evan Dzierzynski

(57) ABSTRACT

A replacement device for a light bulb includes a translucent shell and a base. The base is configured to be received in a conventional light socket. The base also includes a compartment, slot or recess for receiving and securing a replaceable volatile active insert for enabling the device to emit an insect control material when the insert is secured in the compartment Combinations of one or more of a coiled fluorescent light, a plurality of colored LEDs, and an incandescent light source may also provided in the shell as a source of illumination. Thus, a single device is used as a replacement for a conventional light bulb that provides insect control in the form of a cartridge, bottle, mat, tube, sheet, patch etc.

20 Claims, 15 Drawing Sheets

U.S. PATENT DOCUMENTS

| | | | |
|---|---|---|---|
| 1,565,500 A | 12/1925 | Ritter |
| 1,706,939 A | 3/1929 | Rosenthal |
| 1,732,707 A | 10/1929 | Winsboro |
| 1,920,599 A | 8/1933 | Schuh |
| 2,124,543 A | 7/1938 | Clyne |
| 2,143,246 A | 1/1939 | McGary |
| 2,372,371 A | 3/1945 | Eisner |
| 2,435,756 A | 2/1948 | Schlesinger |
| 2,468,164 A | 4/1949 | Brewster |
| 2,469,656 A | 5/1949 | Lienert |
| 2,535,802 A | 12/1950 | Libson |
| 2,694,771 A | 11/1954 | Cox |
| 2,741,812 A | 4/1956 | Tellier |
| 2,741,813 A | 4/1956 | Rubin |
| 2,757,278 A | 7/1956 | Cloud |
| 2,799,166 A | 7/1957 | Leftwich |
| 2,818,770 A | 1/1958 | Cilurzo |
| 2,931,880 A | 4/1960 | Yaffe |
| 3,080,624 A | 3/1963 | Weber, III |
| 3,119,565 A | 1/1964 | Nottingham |
| 3,377,126 A | 4/1968 | Nijland et al. |
| 3,760,179 A | 9/1973 | Addington, Jr. |
| 3,763,347 A | 10/1973 | Whitaker |
| 3,923,458 A | 12/1975 | Moran |
| 3,948,445 A | 4/1976 | Andeweg |
| 4,009,384 A | 2/1977 | Holland |
| 4,045,664 A | 8/1977 | Vrenken et al. |
| 4,184,099 A | 1/1980 | Lindauer et al. |
| 4,234,907 A | 11/1980 | Daniel |
| 4,346,059 A | 8/1982 | Spector |
| 4,391,781 A | 7/1983 | van Lit |
| 4,463,286 A | 7/1984 | Justice |
| 4,493,011 A | 1/1985 | Spector |
| 4,510,555 A | 4/1985 | Mori |
| 4,519,017 A | 5/1985 | Daniel |
| 4,544,592 A | 10/1985 | Spector |
| 4,549,250 A | 10/1985 | Spector |
| 4,561,043 A | 12/1985 | Thompson |
| 4,579,717 A | 4/1986 | Gyulay |
| 4,640,266 A | 2/1987 | Levy |
| 4,647,428 A | 3/1987 | Gyulay |
| 4,647,433 A * | 3/1987 | Spector ........................ 422/125 |
| 4,714,984 A | 12/1987 | Spector |
| 4,754,372 A | 6/1988 | Harrison |
| 4,816,973 A * | 3/1989 | Atalla et al. ................. 362/643 |
| 4,849,181 A | 7/1989 | Kelley et al. |
| 4,849,606 A | 7/1989 | Martens, III et al. |
| 4,875,144 A | 10/1989 | Wainwright |
| 4,885,663 A | 12/1989 | Parker |
| 4,933,815 A | 6/1990 | Parthasarathy |
| 4,955,975 A | 9/1990 | Mori |
| 4,965,490 A | 10/1990 | Ratner |
| 4,965,701 A | 10/1990 | Voland |
| 4,972,305 A | 11/1990 | Blackburn |
| 4,974,136 A | 11/1990 | Noori-Shad et al. |
| 5,021,928 A | 6/1991 | Daniel |
| 5,046,837 A | 9/1991 | Stroomer et al. |
| 5,066,085 A | 11/1991 | Gimbutas et al. |
| 5,069,877 A | 12/1991 | Pozzo |
| 5,178,839 A | 1/1993 | Spector |
| 5,183,323 A | 2/1993 | Daniel |
| 5,217,696 A | 6/1993 | Wolverton et al. |
| 5,247,491 A | 9/1993 | Kwiatkowski |
| 5,249,105 A | 9/1993 | Koizumi |
| 5,251,116 A | 10/1993 | Wijbenga et al. |
| 5,301,090 A | 4/1994 | Hed |
| 5,402,517 A | 3/1995 | Gillett et al. |
| 5,426,474 A | 6/1995 | Rubtsov et al. |
| 5,432,876 A | 7/1995 | Appeldorn et al. |
| D363,537 S | 10/1995 | Moody |
| 5,455,750 A | 10/1995 | Davis et al. |
| 5,547,616 A | 8/1996 | Dancs et al. |
| 5,556,191 A | 9/1996 | Maassen |
| 5,561,346 A | 10/1996 | Byrne |
| 5,568,964 A | 10/1996 | Parker et al. |
| 5,647,052 A | 7/1997 | Patel et al. |
| 5,651,942 A | 7/1997 | Christensen |
| 5,688,042 A | 11/1997 | Madadi et al. |
| 5,691,886 A | 11/1997 | Stacy |
| 5,703,440 A | 12/1997 | Kachmarik et al. |
| 5,711,591 A | 1/1998 | Jordan |
| 5,801,484 A | 9/1998 | Bankuti et al. |
| 5,823,652 A | 10/1998 | Vann |
| 5,908,231 A | 6/1999 | Huff |
| 6,016,038 A | 1/2000 | Mueller et al. |
| 6,099,137 A * | 8/2000 | McCormack et al. ......... 362/96 |
| 6,106,786 A | 8/2000 | Akahoshi |
| 6,120,737 A | 9/2000 | Zembrodt |
| 6,143,313 A | 11/2000 | Ito et al. |
| 6,150,774 A | 11/2000 | Mueller et al. |
| 6,166,496 A | 12/2000 | Lys et al. |
| 6,200,002 B1 | 3/2001 | Marshall et al. |
| 6,211,626 B1 | 4/2001 | Lys et al. |
| 6,217,188 B1 | 4/2001 | Wainwright et al. |
| 6,220,722 B1 | 4/2001 | Begemann |
| 6,220,742 B1 | 4/2001 | Lloyd et al. |
| 6,234,645 B1 | 5/2001 | Borner et al. |
| 6,234,648 B1 | 5/2001 | Borner et al. |
| 6,234,649 B1 | 5/2001 | Katougi |
| 6,254,248 B1 | 7/2001 | McAuley et al. |
| 6,270,720 B1 | 8/2001 | Mandish |
| 6,292,901 B1 | 9/2001 | Lys et al. |
| 6,294,800 B1 | 9/2001 | Duggal et al. |
| 6,299,338 B1 | 10/2001 | Levinson et al. |
| 6,318,876 B1 | 11/2001 | Sigro et al. |
| 6,339,298 B1 | 1/2002 | Chen |
| 6,340,868 B1 | 1/2002 | Lys et al. |
| 6,371,450 B1 | 4/2002 | Davis et al. |
| 6,371,634 B1 | 4/2002 | Tufte |
| D457,667 S | 5/2002 | Piepgras et al. |
| D457,669 S | 5/2002 | Piepgras et al. |
| D457,974 S | 5/2002 | Piepgras et al. |
| 6,391,329 B1 | 5/2002 | Ito et al. |
| D458,395 S | 6/2002 | Piepgras et al. |
| 6,400,104 B1 | 6/2002 | Ham |
| 6,402,347 B1 | 6/2002 | Maas et al. |
| 6,406,172 B1 | 6/2002 | Harbers et al. |
| 6,416,180 B1 | 7/2002 | Strobl |
| D463,610 S | 9/2002 | Piepgras et al. |
| 6,459,919 B1 | 10/2002 | Lys et al. |
| 6,472,876 B1 | 10/2002 | Notohamiprodjo et al. |
| 6,478,440 B1 | 11/2002 | Jaworski et al. |
| 6,478,453 B2 | 11/2002 | Lammers et al. |
| 6,480,649 B2 | 11/2002 | Lee |
| D468,035 S | 12/2002 | Blanc et al. |
| 6,488,393 B1 | 12/2002 | Burnham |
| 6,499,860 B2 | 12/2002 | Begemann |
| 6,513,954 B2 | 2/2003 | Ebersole |
| 6,528,954 B1 | 3/2003 | Lys et al. |
| 6,536,910 B2 | 3/2003 | Lin |
| 6,536,914 B2 | 3/2003 | Hoelen et al. |
| 6,539,656 B2 | 4/2003 | Maas et al. |
| 6,543,925 B2 | 4/2003 | Kuykendal et al. |
| 6,547,416 B2 | 4/2003 | Pashley et al. |
| 6,547,423 B2 | 4/2003 | Marshall et al. |
| 6,548,967 B1 | 4/2003 | Dowling et al. |
| 6,558,022 B2 | 5/2003 | Kawahara |
| 6,573,536 B1 | 6/2003 | Dry |
| 6,577,080 B2 | 6/2003 | Lys et al. |
| 6,586,882 B1 | 7/2003 | Harbers |
| 6,601,982 B1 | 8/2003 | Begemann et al. |
| 6,608,453 B2 | 8/2003 | Morgan et al. |
| 6,613,288 B2 | 9/2003 | Gupte |
| 6,624,597 B2 | 9/2003 | Dowling et al. |

| Patent/Pub No. | Date | Name |
|---|---|---|
| 6,626,554 B2 | 9/2003 | Rincover et al. |
| 6,627,857 B1 | 9/2003 | Tanner et al. |
| 6,628,885 B1 | 9/2003 | Wilkie et al. |
| 6,629,772 B2 | 10/2003 | Brunfeld |
| 6,642,669 B1 | 11/2003 | MacAdam et al. |
| 6,648,486 B2 | 11/2003 | Harbers et al. |
| 6,648,496 B1 | 11/2003 | Elghoroury et al. |
| 6,655,824 B2 | 12/2003 | Tufte |
| 6,672,734 B2 | 1/2004 | Lammers |
| 6,676,282 B2 | 1/2004 | Begemann et al. |
| 6,688,753 B2 | 2/2004 | Calon et al. |
| 6,712,494 B1 | 3/2004 | Hodge |
| 6,717,376 B2 | 4/2004 | Lys et al. |
| 6,720,745 B2 | 4/2004 | Lys et al. |
| 6,726,341 B2 | 4/2004 | Pashley et al. |
| 6,733,161 B2 | 5/2004 | Tufte |
| D491,678 S | 6/2004 | Piepgras et al. |
| D492,042 S | 6/2004 | Piepgras et al. |
| 6,742,914 B2 | 6/2004 | Prodell |
| 6,745,506 B2 | 6/2004 | Maas et al. |
| 6,758,573 B1 | 7/2004 | Thomas et al. |
| 6,774,584 B2 | 8/2004 | Lys et al. |
| 6,777,891 B2 | 8/2004 | Lys et al. |
| 6,779,905 B1 | 8/2004 | Mazursky et al. |
| 6,781,329 B2 | 8/2004 | Mueller et al. |
| 6,788,011 B2 | 9/2004 | Mueller et al. |
| 6,793,360 B2 | 9/2004 | Goslee |
| 6,796,685 B1 | 9/2004 | Nemirow |
| 6,801,003 B2 | 10/2004 | Schanberger et al. |
| 6,802,635 B2 | 10/2004 | Robertson et al. |
| 6,806,659 B1 | 10/2004 | Mueller et al. |
| 6,815,724 B2 | 11/2004 | Dry |
| 6,817,731 B2 | 11/2004 | Tufte |
| 6,831,303 B2 | 12/2004 | Dry |
| 6,833,539 B1 | 12/2004 | Maeda |
| 6,837,591 B2 | 1/2005 | Tufte |
| 6,840,646 B2 | 1/2005 | Cornelissen et al. |
| 6,848,822 B2 | 2/2005 | Ballen et al. |
| 6,851,844 B2 | 2/2005 | Guy |
| 6,854,208 B1 | 2/2005 | Chuang et al. |
| 6,854,854 B2 | 2/2005 | Hoelen et al. |
| 6,854,869 B1 | 2/2005 | Fernandez |
| D503,467 S | 3/2005 | Flashinski et al. |
| 6,869,202 B2 | 3/2005 | Tufte |
| 6,869,204 B2 | 3/2005 | Morgan et al. |
| 6,874,909 B2 | 4/2005 | Vanderschuit |
| 6,880,948 B2 | 4/2005 | Koch et al. |
| 6,883,929 B2 | 4/2005 | Dowling |
| 6,883,931 B2 | 4/2005 | Tufte |
| 6,888,322 B2 | 5/2005 | Dowling et al. |
| 6,890,085 B2 | 5/2005 | Hacker |
| 6,897,624 B2 | 5/2005 | Lys et al. |
| 6,902,301 B2 | 6/2005 | Kieronski |
| 6,921,184 B2 | 7/2005 | Tufte |
| 6,936,978 B2 | 8/2005 | Morgan et al. |
| 6,951,401 B2 | 10/2005 | Van Hees et al. |
| 6,952,079 B2 | 10/2005 | Shiang et al. |
| 6,957,897 B1 | 10/2005 | Nelson et al. |
| 6,965,205 B2 | 11/2005 | Piepgras et al. |
| 6,966,665 B2 | 11/2005 | Limburg et al. |
| 6,976,774 B2 | 12/2005 | Reiss |
| 7,008,096 B1 | 3/2006 | Coushaine et al. |
| 7,038,399 B2 | 5/2006 | Lys et al. |
| 7,046,920 B2 | 5/2006 | Flashinski |
| 7,052,152 B2 | 5/2006 | Harbers et al. |
| 7,067,981 B2 | 6/2006 | Nishio et al. |
| 7,075,224 B2 | 7/2006 | Coushaine |
| 7,080,932 B2 | 7/2006 | Keuper |
| 7,086,756 B2 | 8/2006 | Maxik |
| 7,086,767 B2 | 8/2006 | Sidwell et al. |
| 7,093,958 B2 | 8/2006 | Coushaine |
| 7,104,679 B2 | 9/2006 | Shin et al. |
| 7,109,665 B2 | 9/2006 | Green |
| 7,116,294 B2 | 10/2006 | Stopa |
| 7,160,012 B1 | 1/2007 | Hilscher et al. |
| 7,175,302 B2 | 2/2007 | Kazar et al. |
| 2001/0014019 A1 | 8/2001 | Begemann |
| 2001/0035853 A1 | 11/2001 | Hoelen et al. |
| 2001/0038532 A1 | 11/2001 | Harbers et al. |
| 2001/0049893 A1 | 12/2001 | Maas et al. |
| 2002/0006044 A1 | 1/2002 | Harbers et al. |
| 2002/0030997 A1 | 3/2002 | Tufte |
| 2002/0071285 A1 | 6/2002 | Tufte |
| 2002/0075671 A1 | 6/2002 | Tufte |
| 2002/0075674 A1 | 6/2002 | Tufte |
| 2002/0105800 A1 | 8/2002 | Tufte |
| 2002/0118538 A1 | 8/2002 | Calon et al. |
| 2002/0131273 A1 | 9/2002 | Tufte |
| 2002/0135997 A1 | 9/2002 | Lammers |
| 2002/0136017 A1 | 9/2002 | Tufte |
| 2002/0141058 A1 | 10/2002 | Itoh |
| 2003/0007887 A1 | 1/2003 | Roumpos et al. |
| 2003/0021117 A1 | 1/2003 | Chan |
| 2003/0039115 A1 | 2/2003 | Lin |
| 2003/0046842 A1 | 3/2003 | Maas et al. |
| 2003/0071932 A1 | 4/2003 | Tanigaki |
| 2003/0078791 A1 | 4/2003 | Tufte |
| 2003/0095409 A1 | 5/2003 | Cheng |
| 2003/0209183 A1 | 11/2003 | Tufte |
| 2003/0223230 A1* | 12/2003 | Li ................. 362/216 |
| 2003/0231488 A1 | 12/2003 | Albee |
| 2003/0235601 A1* | 12/2003 | Hallahan ............... 424/405 |
| 2004/0066652 A1 | 4/2004 | Hong |
| 2004/0070967 A1 | 4/2004 | Kennedy |
| 2004/0095078 A1 | 5/2004 | Leong |
| 2004/0095754 A1 | 5/2004 | Hsu |
| 2004/0095780 A1 | 5/2004 | Reed |
| 2004/0109317 A1 | 6/2004 | Ribarich |
| 2004/0124790 A1 | 7/2004 | Han et al. |
| 2004/0179358 A1 | 9/2004 | Tufte |
| 2004/0189218 A1 | 9/2004 | Leong et al. |
| 2004/0212321 A1* | 10/2004 | Lys et al. ............... 315/291 |
| 2004/0232825 A1 | 11/2004 | Sorg |
| 2004/0246711 A1 | 12/2004 | Brenchley et al. |
| 2004/0257798 A1 | 12/2004 | Hart et al. |
| 2004/0264185 A1 | 12/2004 | Grotsch et al. |
| 2005/0024892 A1 | 2/2005 | Cabrera |
| 2005/0030747 A1 | 2/2005 | Bogdal |
| 2005/0036300 A1 | 2/2005 | Dowling et al. |
| 2005/0047127 A1 | 3/2005 | Tutman |
| 2005/0074358 A1 | 4/2005 | Hart et al. |
| 2005/0099108 A1 | 5/2005 | Hofmann et al. |
| 2005/0104503 A1 | 5/2005 | Ellens et al. |
| 2005/0128751 A1 | 6/2005 | Roberge et al. |
| 2005/0162101 A1 | 7/2005 | Leong et al. |
| 2005/0169015 A1 | 8/2005 | Luk et al. |
| 2005/0169643 A1 | 8/2005 | Franklin |
| 2005/0169666 A1 | 8/2005 | Porchia et al. |
| 2005/0169812 A1 | 8/2005 | Helf et al. |
| 2005/0173675 A1 | 8/2005 | Schmidt et al. |
| 2005/0174473 A1 | 8/2005 | Morgan et al. |
| 2005/0185392 A1 | 8/2005 | Walter et al. |
| 2005/0185398 A1 | 8/2005 | Scannell, Jr. |
| 2005/0195598 A1 | 9/2005 | Dancs et al. |
| 2005/0195600 A1 | 9/2005 | Porchia et al. |
| 2005/0207152 A1 | 9/2005 | Maxik |
| 2005/0213342 A1 | 9/2005 | Tufte |
| 2005/0258439 A1 | 11/2005 | Dry |
| 2005/0258440 A1 | 11/2005 | Dry |
| 2005/0259416 A1 | 11/2005 | Gauna et al. |
| 2005/0265018 A1 | 12/2005 | Yasuda et al. |
| 2005/0265023 A1 | 12/2005 | Scholl |
| 2005/0269581 A1 | 12/2005 | Dry |
| 2005/0275626 A1 | 12/2005 | Mueller et al. |
| 2005/0281030 A1 | 12/2005 | Leong et al. |
| 2005/0285538 A1 | 12/2005 | Jaworski et al. |

| | | | | | | |
|---|---|---|---|---|---|---|
| 2006/0001677 A1 | 1/2006 | Webb et al. | | 2006/0176690 A1 | 8/2006 | Yuen |
| 2006/0002102 A1 | 1/2006 | Leonard | | 2006/0220990 A1 | 10/2006 | Coushaine et al. |
| 2006/0002110 A1 | 1/2006 | Dowling et al. | | 2006/0226795 A1 | 10/2006 | Walter et al. |
| 2006/0006784 A1 | 1/2006 | Takahara et al. | | 2006/0238136 A1 | 10/2006 | Johnson, III et al. |
| 2006/0022214 A1 | 2/2006 | Morgan et al. | | 2006/0244000 A1 | 11/2006 | Jager et al. |
| 2006/0023447 A1 | 2/2006 | Justel et al. | | 2006/0248783 A1 | 11/2006 | Lindquist et al. |
| 2006/0045818 A1* | 3/2006 | Moreland ................... 422/125 | | 2006/0275040 A1 | 12/2006 | Franklin |
| 2006/0055315 A1 | 3/2006 | Bokor et al. | | 2007/0109814 A1* | 5/2007 | Logan ........................ 362/643 |
| 2006/0071589 A1 | 4/2006 | Radkov | | | | |
| 2006/0081871 A1 | 4/2006 | Streubel | | | | |
| 2006/0082333 A1 | 4/2006 | Laski | | | | |
| 2006/0083013 A1 | 4/2006 | Wanninger et al. | | | | |
| 2006/0103291 A1 | 5/2006 | Ellens et al. | | | | |
| 2006/0114670 A1 | 6/2006 | Ho | | | | |
| 2006/0120080 A1 | 6/2006 | Sipinski et al. | | | | |

FOREIGN PATENT DOCUMENTS

| | | |
|---|---|---|
| WO | WO 01/78488 A2 | 10/2001 |
| WO | WO 2004/068945 A1 | 8/2004 |
| WO | WO 2004/073399 A1 | 9/2004 |

* cited by examiner

COMBINATION LIGHT DEVICE WITH INSECT CONTROL INGREDIENT EMISSION

CROSS-REFERENCE TO RELATED APPLICATIONS

This application is a continuation-in-part of U.S. patent application Ser. No. 11/426,055, filed Jun. 23, 2000 now U.S. Pat. No. 7,318,659 which is a continuation-in-part of U.S. patent application Ser. No. 11/069,964, filed on Mar. 3, 2005, now U.S. Pat. No. 7,246,919 which claims priority to Provisional Patent Application Ser. No. 60/549,154, filed on Mar. 3, 2004. This application is also a continuation-in-part of U.S. patent application Ser. No. 10/561,822, filed on Apr. 25, 2006 still pending, which claims priority to Provisional Patent Application Ser. No. 60/483,913 filed on Jul. 2, 2003.

BACKGROUND

1. Technical Field

A substitute for a conventional light bulb is disclosed which provides various combinations of features including, but not limited to, insect control material emission, white light, and colored light in the form of changing colored light shows. The disclosed device screws into a conventional light socket and the insect control ingredient is dispensed from replaceable inserts

2. Description of the Related Art

Creating a pleasant ambience is an important aspect of home decor, both indoors and outdoors. Part of a successful ambiance is achieved through various lighting techniques. The use of various colored lights and color changing light fixtures for mood lights and outdoor light systems is known.

However, a need exists for the combination of white light and/or colored light with volatile active emission in addition to fragrances such as the controlled release of insect repellent, insect attractant, insecticide (any of which may be combined with fragrant materials if necessary to make the ambient environment mote enjoyable).

Biting insects, such as mosquitoes, are annoying and can carry disease. The most well-known mosquito transmitted disease is malaria, which has been an epidemic for decades in many parts of the world Reports arc on the rise of mosquito transferred West Nile various in regions outside of Africa, including North America West Nile virus is spread by the bite of an infected mosquito, and can infect people, horses, many types of birds, and some other animals. On some occasions, a West Nile virus infection can result in severe and sometimes fatal illnesses Other mosquito spread diseases include dengue fever and Eastern Equine Encephalitis (EEE).

Known devices used to attempt to destroy or repel insects include two general types: electric bug zappers and electronic repellers. Many bug zappers rely upon ultraviolet light to draw insects through an electrified wire grid. A burst followed by crackling sounds signals that the insect has passed through the electrocuting grid. Bug zappers may kill many insects, but few of the insects killed are mosquitoes or other pests problematic to humans because mosquitoes are not attracted to light Instead, mosquitoes are attracted to the release of carbon dioxide from a nearby breathing human or animal. In contrast, most of the insects susceptible to bug zappers are beetles or night-flying moths tricked into the trap while attempting to navigate by the moon. Unfortunately, these insects are not problematic to humans. Electronic repellers, that rely on noise or sound waves, have been shown to be ineffective in preventing mosquitoes from biting nearby humans. Some bug zappers and electronic repellers have been augmented with a carbon dioxide source to increase their effectiveness against mosquitoes.

Thus, to control mosquitoes and other biting insect pests problematic to humans, certain chemicals are used, which have been found to be effective at inhibiting the ability of a mosquito to detect a human target. Certain chemicals are effective when applied directly to skin, such at DEET (N,N-diethyl-3-methylbenzamide), the active ingredient in OFF® and other insect repellant brands.

However, many situations make the direct application of insect repellent undesirable, such as during outdoor social parties where people dress expensively or in more formal clothing. In such situations, safe insect repellents can be dispersed in the local ambient area to protect the area from the presence of mosquitoes. One popular type of repellent suitable for such a local distribution is the family of pyrethroid compounds.

Thus, there is a need for devices that distributes such safe insect control chemicals and that also can provide pleasant, ambiance-enhancing lighting.

SUMMARY OF THE DISCLOSURE

In view of the limited options and drawbacks of the lighting and insect control delivery devices currently on the market, devices are disclosed herein which provide various combinations of lighting and the emission of volatile insect control agents.

In one embodiment, a combination light and volatile active dispenser device is provided that comprises a male base for engaging a light socket The base is coupled to a light source and a housing. The housing accommodates a replaceable insert comprising an insect control material In a refinement, the light source comprises a coiled fluorescent light (CFL)

In a refinement, the light source comprises a plurality of colored lights and the device further comprises a control circuitry comprising a memory with at least one colored light show stored in the memory.

In a related refinement, the control circuitry comprises a dimmable electronic ballast for adjusting an intensity level of the CFL In a refinement, the insect control material comprises at least one material selected from the group consisting of (3-phenoxyphenyl)methyl 3-(2,2-dichloroethenyl)-2,2-dimethylcyclopropanecarboxylate; (2-methyl[1,1'-biphenyl]-3-yl)methyl 3-(2-chloro-3,3,3-trifluoro-1-propenyl)-2,2-dimethylcyclopropanecarboxylate; (S)-2-methyl-4-oxo-3-(2-propynyl)-2-cyclopenten-1-yl 2,2-dimethyl-3-(2-methyl-1-propenyl)cyclopropanecarboxylate; 2-methyl-4-oxo-3-(2-propenyl)-2-cyclopenten-1-yl 2,2-dimethyl-3-(2-methyl-1-propenyl)cyclopropanecarboxylate; [1R-[1a(S*),3b]]-2-methyl-4-oxo-3-(2-propenyl)-2-cyclopenten-1-yl 2,2-dimethyl-3-(2-methyl-1-propenyl) cyclopropanecarboxylate; (1,3,4,5,6,7-hexahydro-1,3-dioxo-2H-isoindol-2-yl)methyl 2,2-dimethyl-3-(2-methyl-1-propenyl)cyclopropanecarboxylate; (1,3,4,5,6,7-hexahydro-1,3-dioxo-2H-isoindol-2-yl)methyl (1R)-cis-trans-2,2-dimethyl-3-(2-methyl-1-propenyl)cyclopropanecarboxylate and mixed stereoisomers; (3-phenoxyphenyl)methyl 2,2-dimethyl-3-(2-methyl-1-propenyl)cyclopropanecarboxylate and mixed stereoisomers; [2,3,5,6-tetrafluoro-4-(methoxymethyl)phenyl]methyl 2,2-dimethyl-3-(1-propenyl)cyclopropanecarboxylate; (2,3,5,6-tetrafluoro-4-methylphenyl)methyl 2,2-dimethyl-3-(1-propenyl)cyclopropanecarboxylate; [2,3,5,6-tetrafluoro-4-(methoxymethyl)phenyl]methyl 2,2- dimethyl-3-(2-methyl-1-propenyl)cyclopropanecarboxylate; (1R-trans)-(2,3,5,6-tetrafluorophenyl)methyl 3-(2,2-dichloroethenyl)-2,2-dimethylcyclopropanecarboxylate; [2,5-dioxo-3-(2-propynyl)-1-imidazolidinyl]methyl 2,2-dimethyl-3-(2-methyl-1-propenyl)cyclopropanecarboxylate; 1-ethynyl-2-methyl-2-pentenyl (1R)-cis trans-2,2-dimethyl-3-(2-methyl-1-propenyl)cyclopropanecarboxylate; 2,2-dichloroethenyl dimethyl phosphate; [1a,3a(Z)]-(±)-(2,3,5,6-tetrafluoro-4-methylphenyl)methyl 3-(2-chloro-3,3,3-trifluoro-1-propenyl)-2,2-dimethylcyclopropanecarboxylate; ((R)-trans isomers)-(3-phenoxyphenyl)methyl 2,2-dimethyl-3-(2-methyl-1-propenyl) cyclopropanecarboxylate; cyano(3-phenoxyphenyl)methyl 3-(2,2-dichloroethenyl)-2,2-dimethylcyclopropanecarboxylate; 1-[[2-(4-ethoxyphenyl)-2-methylpropoxy]methyl]-3-phenoxybenzene; 1-methylpropyl 2-(2-hydroxyethyl)-1-piperidinecarboxylate; N,N-diethyl-m-toluamide; and mixtures thereof The common names of the above volatile insect control agents that may be used with the devices disclosed herein include, but are not limited to: permethrin; bifenthrin; prallethrin; allethrin; esbiothrin; tretramethrin; d-tetramethrin; phenothrin; metofluthrin; profluthrin; dimefluthrin; transfluthrin; imiprothrin; empenthrin; dichlorvos; tetfluthrin; phenothrin; cypermethrin; etofenprox; pacardin; n,n-diethyl-m-toluamide; and mixtures thereof.

The term "replaceable insert" is used quite broadly and can take many forms. In yet other related refinements, the replaceable insert is provided in the form of coded sheets of paper or other substrate material, which may be transparent, translucent, or opaque, or impregnated honeycomb structures such as honeycomb cardboard-type structures have also been used to successfully. In one refinement, the replaceable insert comprises a cartridge and the housing comprises a slot for receiving the cartridge, the cartridge containing the insect control material The "cartridge" may be in the form of a plastic cartridge, a tube or bottle with some sort of frangible seal that is broken upon insertion of the cartridge into the housing.

In other refinements, the replaceable insert comprises a mat, sand core or substrate impregnated with the insect control material and the housing comprises a slot for receiving the mat or substrate.

In a refinement, wherein the housing comprises at least one vent for releasing the insect control material.

In a refinement, wherein the device further comprises a fan disposed within the housing and directed at the insert and the housing comprises at least one vent for releasing the insect control material.

In a refinement, the device further comprises a heating element disposed within the housing for volatilizing the insect control material of the insert and the housing comprises at least one vent for releasing the insect control material In a related refinement, a combination of a fan and heating element may be employed.

In another related refinement, the device include a timer so that the insect control material or materials is released during time periods where the insects are most problematic.

In some refinements, the heat source is provided primarily by light source or light sources. In other refinements, heaters are used when the light source or sources are turned off. And still other refinements, heaters or heat sources are used in combination with light or light sources. In yet another refinement, the device includes a photocell and a battery system that provides energy to a heater at dusk or at night. Various combinations of photocells and timers may be employed and are considered within the scope of this disclosure Timers may also be employed to cycle on and off to thereby conserve the insect control material.

In a refinement, the light source comprises a low voltage white light source

In yet another refinement, the means for distributing the insect controlled material is a piezo aerosol system Such systems can be built in a compact manner and can serve as a substitute for a fan.

Thus, a device is disclosed which provides two important functions, either of which may be more important depending upon the location or country A single device provides ambiance-enhancing lighting and effective insect control material dispertion Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiment illustrated in greater detail on the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

Figure 1:
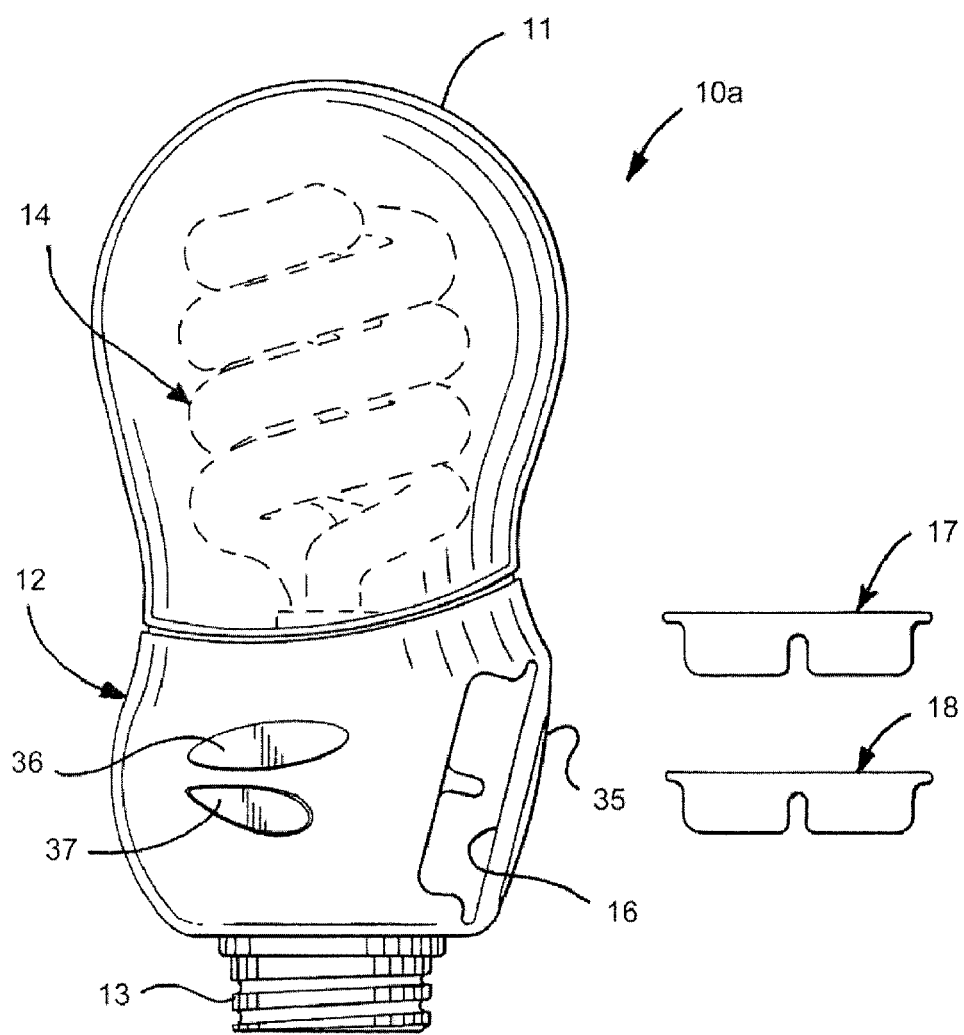
FIG. 1 is a side plan view of a disclosed combination white light/insect control vapor emission device with a threaded, screw-in base.
Figure 2:
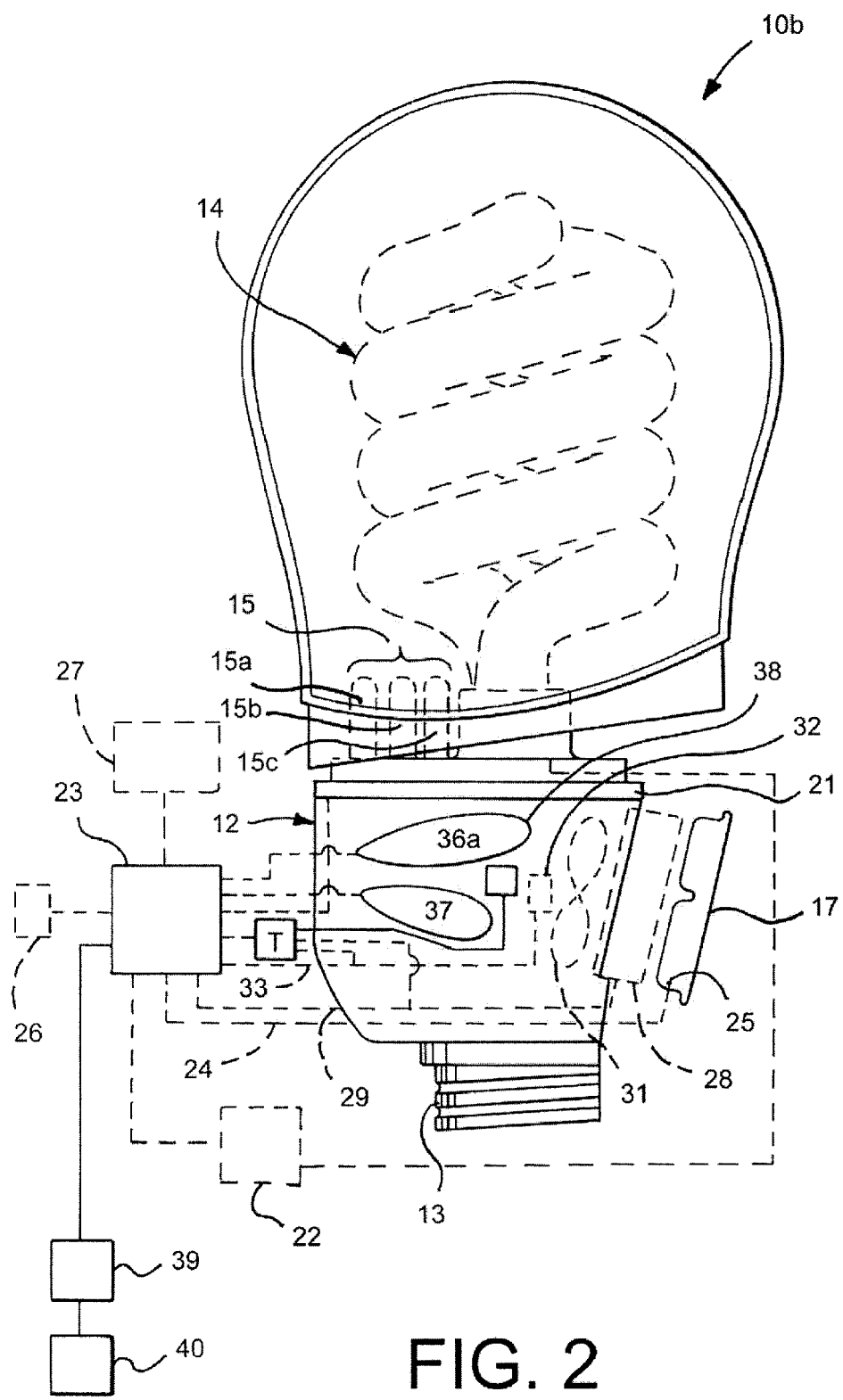
FIG. 2 is a partial side plan/cross-sectional/schematic view of another device with a threaded, screw-in base, but including at this least one RGB LED light cluster for producing colored light in addition to or instead of white light and various means for enhancing the emission of the active material as well as associated control circuitry.
Figure 3:
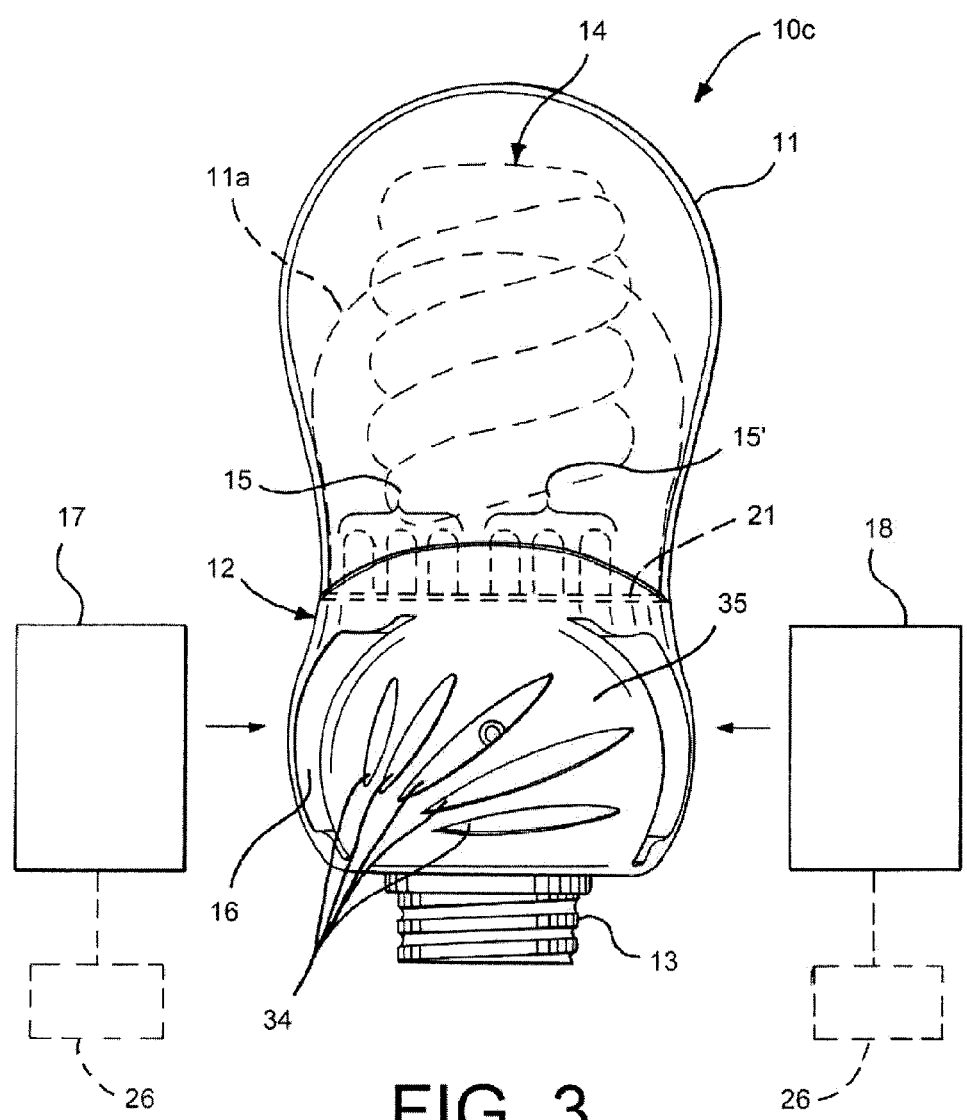
FIG. 3 is a front plan view of an insect control vapor emission device particularly illustrating a first option for device with a plurality of RGB LED light clusters for colored lighting, wherein the RGB LED clusters are shown in phantom with a smaller outer shell as well as another option that may include a coiled fluorescent lamp (CFL, also shown in phantom) with or without one or more RGB LED light cluster(s), including the possibility of two active inserts (e g, insect repellant and fragrance), with the possibility of memory chips associated with the inserts.

FIGS. 1-3 illustrate screw-in combination white light and/or colored light show and insect control material emission device 10a-10c made in accordance with this disclosure. While the disclosed devices can mate with any one of a number of lighting fixtures (such as conventional fixtures for receiving incandescent, halogen, or fluorescent bulbs), for exemplary purposes, the description provided herein refers to an Edison-style, screw-in light device that mates with a conventional incandescent light socket with a threaded female receptacle. Of course, the devices of this disclosure may be embodied in any light bulb that mates with a light socket/power source. The devices 10a-10c are not limited to Edison style sockets. The devices 10a-10c obviously can be used in all types of light sockets, used worldwide Thus, the connector 13 may be threaded, or of a twist and lock type, depending upon the country or region where used. The devices 10a-10c may be used indoors or outdoors.

Device 10a of FIG. 1 includes a translucent housing or cover 11 mounted onto a base 12. The bottom of base 12 comprises, in this case a threaded male, screw-in connector 13, which is configured to mate with a threaded female socket of a conventional lamp or other lighting fixture (i.e., Edison-type receptacle). When the connector 13 is mated with such a socket, AC power is provided to the device 10 from the lamp or lighting fixture, again which may be indoors or outdoors. Of course, DC powered devices, including low voltage DC devices, are considered within the scope of this disclosure.

In the embodiment 10a shown in FIG. 1, a white light source is provided in the form of coiled fluorescent lamp or compact fluorescent lamp (CFL) 14. As shown in FIG. 2 and the embodiment 10b, the white light source 14 may be combined with a red/green/blue (RGB) light emitting diode (LED) cluster 15 with individual LEDs 15a, 15b, 15c Returning to FIG. 1, the device 10a includes a slot or receiving area 16 for receiving one or more cartridges 17, 18 The cartridges 17, 18 may both include insect control material or one of the cartridges 17, 18 may include insect control material and at the second of the cartridges 17, 18 may include a fragrance or other volatile active. The cartridges 17, 18 may be provided in almost any form that can be inserted into the slot 16. Another option is to utilize a solid mat-type structure or substrate that is impregnated with insect control material as disclosed, for example, in commonly assigned U.S. Pat. Nos. 7,046,920 and 6,551,560, both of which are incorporated herein by reference. One type of exemplary cartridge 17 or 18 is disclosed in U.S. Pat. No. 4,849,606 and, as another alternative, impregnated substrates such as "sand core" tablets or other types of structures as disclosed in "WO 2004/068945 maybe employed Both of these references are also incorporated herein by reference. The active may also be impregnated into thin sheets of paper or other substrates that maybe transparent, translucent or opaque. Honeycomb structures, such as cardboard honeycomb structures impregnated with active material may also be employed.

Figure 7:
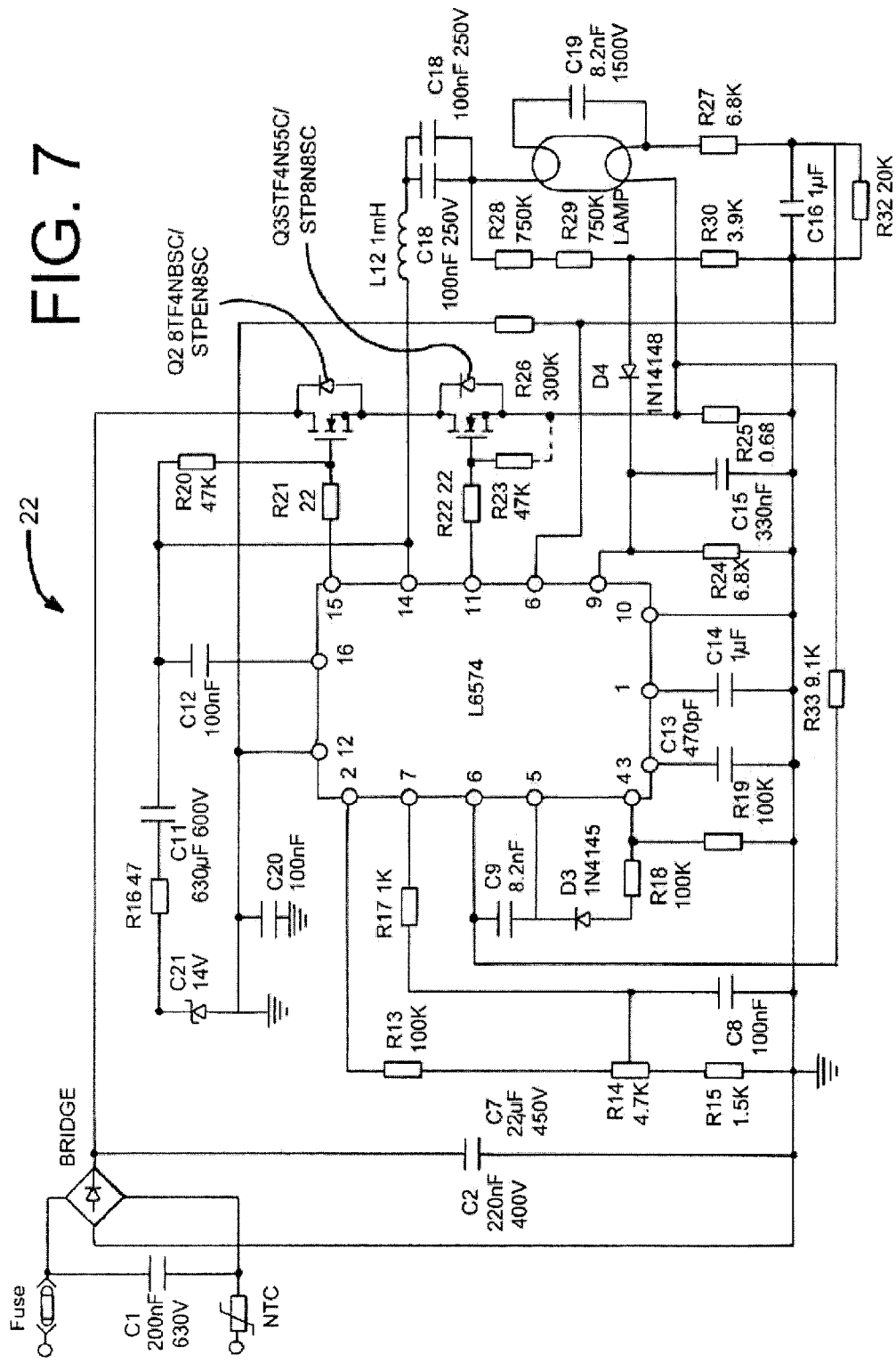
FIG. 7 is a circuit diagram for a dimmable ballast for the coiled fluorescent lamp (CFL) of the devices shown in FIGS. 1-3.

Turning to FIG. 2, the alternative device 10b, like the other devices 10a (FIG. 1), 10c (FIG. 3), includes a circuit board 21, which provides a variety of functions, including delivering power to the CFL 14. Preferably, the CFL 14 is equipped with an appropriate electronic ballast 22, a one example of which is illustrated in FIG. 7, which discloses a "dimmable" electronic ballast Returning to FIG. 2, a microprocessor or controller 23 is also mounted on the board 21. The controller 23 may include a link 24 to the cartridge 17, the end of which may include a sensor 25 for generating a use-up cue by the controller 23. The use-up cue may be in the form of a flashing light signal or audible sound.

The controller 23 also operates the LED cluster 15, should colored lights be included in the embodiment. An optional memory 26 may be included to provide a wider variety of colored light shows that will be discussed in greater detail below. If used outdoors with other similar devices, the controller 23 may also be linked to a network card and 27 to coordinate light shows and rates of insect control material emission In FIG. 2, four means for volatilizing the insect control material and/or fragrance are disclosed First a heating element 28 may be disposed in close proximity to the cartridge/mat 17 to enhance volatilization The heating element 28, which may be a simple resistance device, is linked to the controller 23 and or timer T as shown at 29. The heating element may also be linked to a time T so that the active may be released at or the rate of release increased during periods where mosquitoes are active, e g, at dusk. Second, instead of or in supplementation to the heating element 28, a fan 31 may be employed with a motor 32 which, in turn, is linked to the controller 23 and or time T as shown at 33 Third, depending upon the insect control material utilized, ambient air flow may be sufficient to achieve a desired release rate. Thus, as seen in FIG. 3, a plurality of vents 34 or a single vent 34 may be provided in the front plate 35 of the base 12. A piezoelectrically actuated atomization device 38 may also be employed as disclosed in U.S. Pat. Nos. 7,070,121, 7,007, 861, and 6,896,193, which are incorporated herein by reference. Finally, it will be noted here that heat from the white light source 14 and/or heat from the colored light sources 15 may provide sufficient heat for satisfactory emission rates for many volatile actives.

Figure 4:
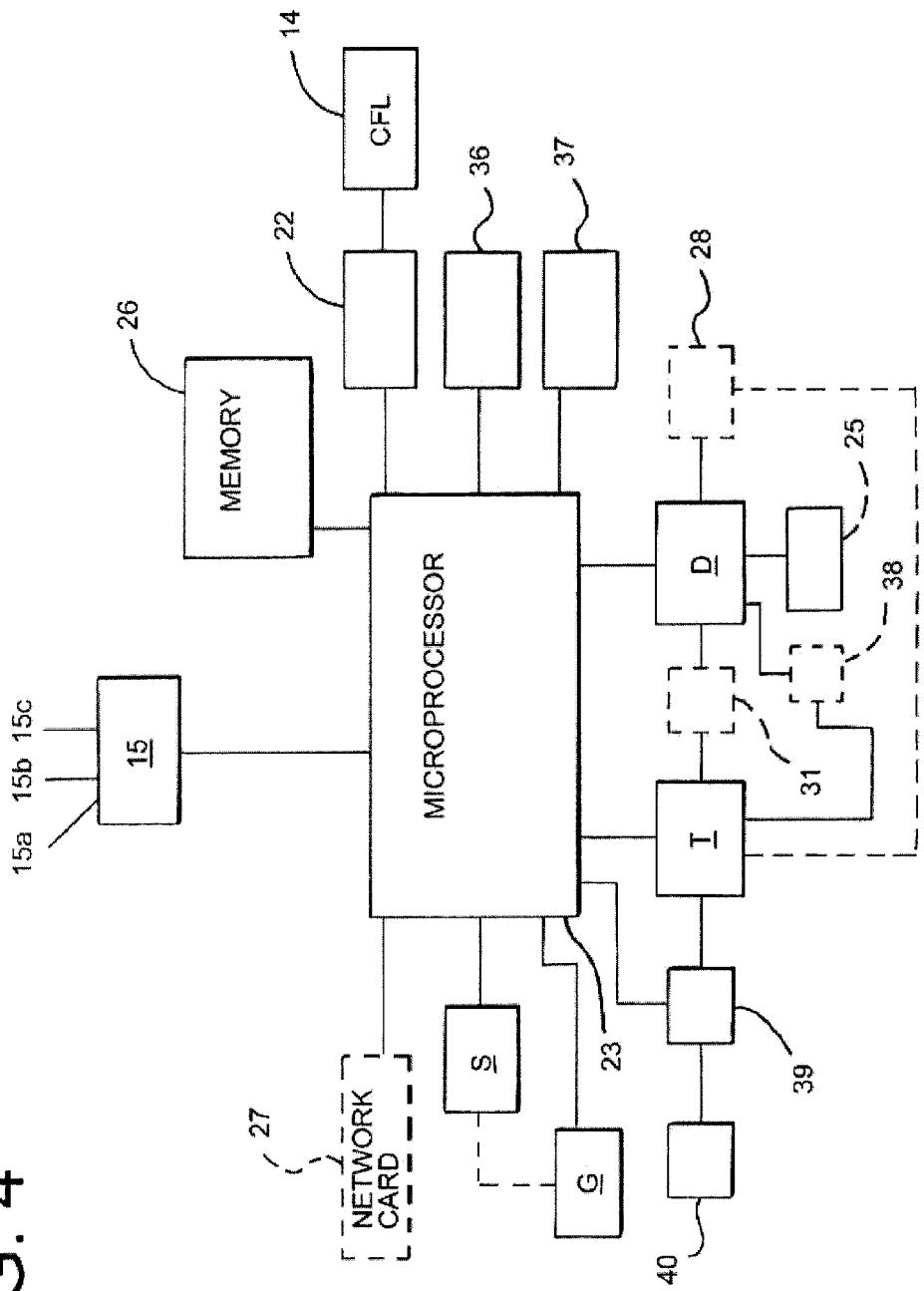
FIG. 4 schematically illustrates functional units of the devices illustrated in FIGS. 1-3.

The heater 28 can be provided in the form of a metal oxide resistor or wire wound resistor potted in a ceramic block Of course, other heating devices may be used for the heater 28, such as a PTCR (Positive Temperature Coefficient Resistor) heater, a coil resistance heater, printed circuitry, an etched foil heating device, or the like. When in use, heater 28 generates heat for heating the active ingredient of liquid or gel formulations stored in a cartridge, mat, bottle, sheet, etc 17, 18. Such arrangements of heat-assisted evaporation devices are known in the art, and will not be described in detail herein. In general, it the active containing elements 17, 18 contain a formulation/active ingredient whose evaporation rate increases with the application of heat, the evaporation rate (and consequently, the potency) can be controlled as the heat is varied by the controller 23. As shown in FIGS. 2 and 4, a solar photovoltaic cell may be employed with a battery 40.

Two control buttons 36, 37 are provided in the embodiments illustrated in this disclosure and are linked to the controller 23 However, as will be apparent to one skilled in the art, a single control button, or more than two control buttons may be employed, all of which depend upon the particular features of the devices and the programming of the controller 23.

Turning to FIG. 3, the versatility of the design of this disclosure is particularly illustrated. As shown in FIG. 3, the device 10c may include a CFL 14 with or without colored lighting capability. Further, the device 10c may include colored lighting capability in the form of multiple LED clusters 15, 15'. While only two clusters 15, 15' are illustrated in FIG. 3, it will be noted that only a single cluster or more than two clusters may be employed. A smaller outer shell 11a is shown in phantom in the event a smaller device without a CFL 14 is desired.

The RGB LED clusters may be operated in any one of a number of combinations to provide a specific color of light, color shows or patterns that are pleasing to a user. For example, the LEDs may be operated as described in commonly assigned International Publication No. WO2005/003625, US Publication Nos. US 2005/0169812 and US 2005/0169666, all of which are incorporated herein by reference. The outer shell 11, 11a may act as a light diffuser, to cause a user to perceive the intended color, rather than the activation of distinct LEDs of different colors. The lighting effects may also be programmed to attract or repel insects, using conventionally known lighting techniques for the same. The shell or diffuser 11, 11a may also act is a fragrance/insect repellent dispenser as the walls of the diffuser 11 may absorb fragrance or other active ingredients or the diffuser 11 may include inner and outer walls with a void space therebetween that accommodates insect control material and/or fragrance.

Still referring to FIG. 3, the white LEDs 15 can provide a primary source of illumination for the device 10c but the CFL 14 may be needed where higher levels of illumination are desired. Alternatively (or in addition), the red, green, and blue LEDs 15, 15' may be configured to, in combination, produce white light as illustrated below in FIG. 6, or when their respective wavelengths are mixed by a diffuser/shell 11 or the like Examples of a RGB LED cluster producing white light can be found in commonly assigned Provisional Application No. 60/641,441, which is incorporated herein by reference. Other conventional light sources, such as halogen or other types of fluorescent lights may also be used as a primary light source.

Figure 12:
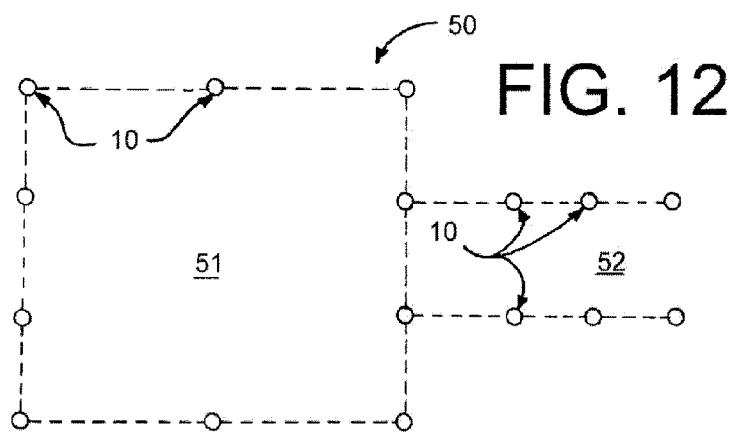
FIG. 12 is a schematic illustration of the disclosed devices used in an outdoor area such as a patio and/or walkway.

Regarding the use of insect control actives, the disclosed devices may be particularly useful for patio/deck lighting and outdoor perimeter lighting where it is desirable to keep insects away from a defined area such as a patio, deck or pool area and/or where it is desirable to attract insects away from such a defined area as shown in FIG. 12. Still further, use of the disclosed devices in an enclosed area such as the closet provides the opportunity for the volatile active to be a moth, cockroach, housefly, fruit fly, ant, gnat or other household insect killer or repellent Therefore, an ingredient suitable for inclusion in the evaporative cartridges, bottles, mats, packages, tubes, sheets, substances, honeycomb structures, etc disclosed herein, or passive dispensers disclosed herein, in addition to insect repellents, attractants and insecticides is a fragrance, air freshener, deodorizer, odor eliminator, disinfectant, sanitizer or malodor counteractant, or the like, in liquid, oil or gel form, although gels and oils are preferred.

The insect control material used with the disclosed devices includes, but is not limited to the following: (3-phenoxyphenyl)methyl 3-(2,2-dichloroethenyl)-2,2-dimethylcyclopropanecarboxylate; (2-methyl[1,1'-biphenyl]-3-yl)methyl 3-(2-chloro-3,3,3-trifluoro-1-propenyl)-2,2-dimethylcyclopropanecarboxylate; (S)-2-methyl-4-oxo-3-(2-propynyl)-2-cyclopenten-1-yl 2,2-dimethyl-3-(2-methyl-1-propenyl)cyclopropanecarboxylate; 2-methyl-4-oxo-3-(2-propenyl)-2-cyclopenten-1-yl 2,2-dimethyl-3-(2-methyl-1-propenyl) cyclopropanecarboxylate; [1R-[1a(S*),3b]]-2-methyl-4-oxo-3-(2-propenyl)-2-cyclopenten-1-yl 2,2-dimethyl-3-(2-methyl-1-propenyl)cyclopropanecarboxylate; (1,3,4,5,6,7-hexahydro-1,3-dioxo-2H-isoindol-2-yl)methyl 2,2-dimethyl-3-(2-methyl-1-propenyl) cyclopropanecarboxylate; (1,3,4,5,6,7-hexahydro-1,3-dioxo-2H-isoindol-2-yl)methyl (1R)-cis trans-2,2-dimethyl-3-(2-methyl-1-propenyl)cyclopropanecarboxylate and mixed stereoisomers; (3-phenoxyphenyl)methyl 2,2-dimethyl-3-(2-methyl-1-propenyl)cyclopropanecarboxylate and mixed stereoisomers; [2,3,5,6-tetrafluoro-4-(methoxymethyl)phenyl]methyl 2,2-dimethyl-3-(1-propenyl)cyclopropanecarboxylate; (2,3,5,6-tetrafluoro-4-methylphenyl)methyl 2,2-dimethyl-3-(1-propenyl)cyclopropanecarboxylate; [2,3,5,6-tetrafluoro-4-(methoxymethyl)phenyl]methyl 2,2-dimethyl-3-(2-methyl-1-propenyl)cyclopropanecarboxylate; (1R-trans)-(2,3,5,6-tetrafluorophenyl)methyl 3-(2,2-dichloroethenyl)-2,2-dimethylcyclopropanecarboxylate; [2,5-dioxo-3-(2-propynyl)-1-imidazolidinyl]methyl 2,2-dimethyl-3-(2-methyl-1-propenyl)cyclopropanecarboxylate; 1-ethynyl-2-methyl-2-pentenyl (1R)-cis-trans-2,2-dimethyl-3-(2-methyl-1-propenyl)cyclopropanecarboxylate; 2,2-dichloroethenyl dimethyl phosphate; [1a,3a(Z)]-(±)-(2,3,5,6-tetrafluoro-4-methylphenyl)methyl 3-(2-chloro-3,3,3-trifluoro-1-propenyl)-2,2-dimethylcyclopropanecarboxylate; ((R)-trans isomers)-(3-phenoxyphenyl)methyl 2,2-dimethyl-3-(2-methyl-1-propenyl) cyclopropanecarboxylate; cyano(3-phenoxyphenyl)methyl 3-(2,2-dichloroethenyl)-2,2-dimethylcyclopropanecarboxylate; 1-[[2-(4-ethoxyphenyl)-2-methylpropoxy]methyl]-3-phenoxybenzene; 1-methylpropyl 2-(2-hydroxyethyl)-1-piperidinecarboxylate; N,N-diethyl-m-toluamide; and mixtures thereof.

The common names of the above volatile insect control agents that may be used with the devices disclosed herein include, but are not limited to: permethrin; bifenthrin; prallethrin; allethrin; esbiothrin; tretramethrin; d-tetramethrin; phenothrin; metofluthrin; profluthrin; dimefluthrin; transfluthrin; imiprothrin; empenthrin; dichlorvos; tetfluthrin; phenothrin; cypermethrin; etofenprox; pacardin; n,n-diethyl-m-toluamide; and mixtures thereof If a fragrance is to be dispensed, the fragrance or air freshener is a fragrance comprising one or more volatile organic compounds which are available from perfumery suppliers such as Firmenich Inc, Takasago Inc., Noville Inc, Quest Co., International Flavors & Fragrances, and Givaudan-Roure Corp. Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like A fragrance can be relatively simple in composition, or can be a complex mixture of natural and synthetic chemical components. Synthetic types of fragrance compositions either alone or in combination with natural oils are described in U.S. Pat. Nos. 4,324,915, 4,411,829; and 4,434,306, which are incorporated herein by reference. Other artificial liquid fragrances include geraniol, geranyl acetate, eugenol, isoeugenol, linalool, linalyl acetate, phenethyl alcohol, methyl ethyl ketone, methylionone, isobomyl acetate, and the like.

A thixotropic gel for the insect control material or the fragrance may be formed by the addition of a thickening agent, such as a cellulosic material, a polymeric thickener, or a fumed silica of the type marketed under the Cabosil trademark by Cabot Corporation. An insect control material or fragrance ingredient can also be in the form of a crystalline solid, which has the ability to sublime into the vapor phase at ambient or elevated temperatures.

FIG. 4 shows a diagrammatic representation of functional units of the devices 10a, 10b, 10c of FIGS. 1-3. Microcontroller 23 is a programmable controller that produces output signals to control the emission of light from the LEDs 15a-15c (FIG. 2), 15a-15c, 15a'-15c'(FIG. 3) of a light array 15, 15'. As seen by the coupling or wiring 24, 29, 33 in FIG. 2, the microcontroller 23 also controls the amount of active emitted from the cartridges or mats 17, 18 The microcontroller 23 also initiates the operation of the ballast 22 for the CFL 14.

Still referring to FIG. 4, the microprocessor 23 may be linked to additional memory 26 which may be in the form of a memory card that can be placed or provided with the cartridges 17, 18 as shown schematically in FIG. 3 The data stored in the additional memory 26 may include colored light shows, variations in dispense rates for additional reprogramming capabilities. The dispensing assembly D of FIG. 4 may include any one or more of a fan 31, heater 28 and use-up cue 25. A timer T and a sensor S may also be included and linked to the controller 23 as explained in greater detail below. In remote areas where electricity is not available or expensive, a photovoltaic cell 39 and battery 40 may also be employed Alternatively, one or mote of the control features may be mechanically set by a user, without the assistance of a microprocessor. Such basic controls would be readily understood by one of ordinary skill in the art. Preferably, however, microcontroller 23 produces and outputs the signals to operate these devices according to one or more programs stored in the memory 26 or communicated to the controller 23 via the network card 27. The programs may be preset in the memory 26 and then selected and activated by a user through a user interface (e g, switches 36, 37). The signals may be in the form of voltages, coded pulses, or other signals, which control the operation of the components shown in FIGS. 2 and 4

Operation of microcontroller 23 can also be activated to produce a presentation according to a signal from sensor S Sensor S may include, for example, a motion sensor, a sound sensor, a timing sensor, an infrared sensor, a power source-monitoring sensor, temperature sensor, $CO_2$ sensor or the like. If a power source-monitoring sensor is used, the microcontroller 23 may be configured to activate and/or change the presentation of light and/or active emission rate when a power switch of a light socket or lamp in which the bulb is received is toggled (e g, one toggle activates the fluorescent light source 14, two toggles in succession activates the LED array 15, etc.)

A carbon dioxide sensor could be employed to increase insect repellent, attractant or insecticide when $CO_2$ ppm increase is due to the presence of a human user. A carbon dioxide generator (could be employed to increase the amount of carbon dioxide it generates when the presence of people are detected to attract tests to the device 10a-10c instead of the humans.

The devices 10a-10c may also include a timing mechanism T The timing mechanism T may be an oscillator, crystal, conventional clock, etc The timing mechanism T may control the operation of microcontroller 23 in accordance with the program from the memory 26. In addition, the timing mechanism T may be used to control the length of a presentation of light, and/or repellent emission rate set by a program in memory 26, as programmed by a user. Further, in the case where a memory card 26 is disposed on the active ingredient device 17 or 18 (see FIG. 3), the memory card 26 may contain temperature information that is communicated to the microprocessor 23 that, in turn, is used to set the optimum temperature for that active optimize release of the active.

Figure 5A:
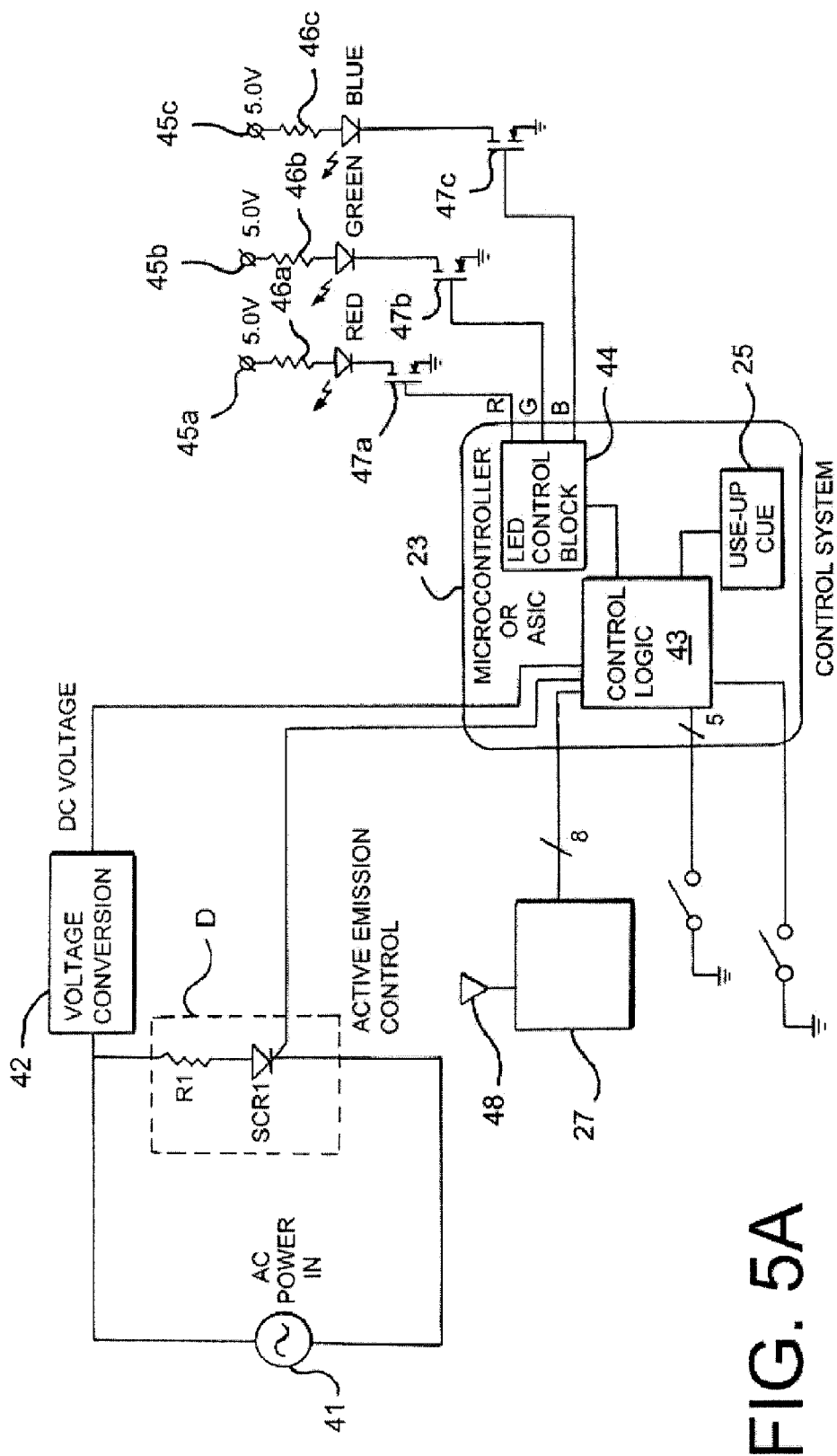
FIG. 5A is a circuit diagram illustrating control mechanisms for the devices shown in FIGS. 1-4.
Figure 5B:
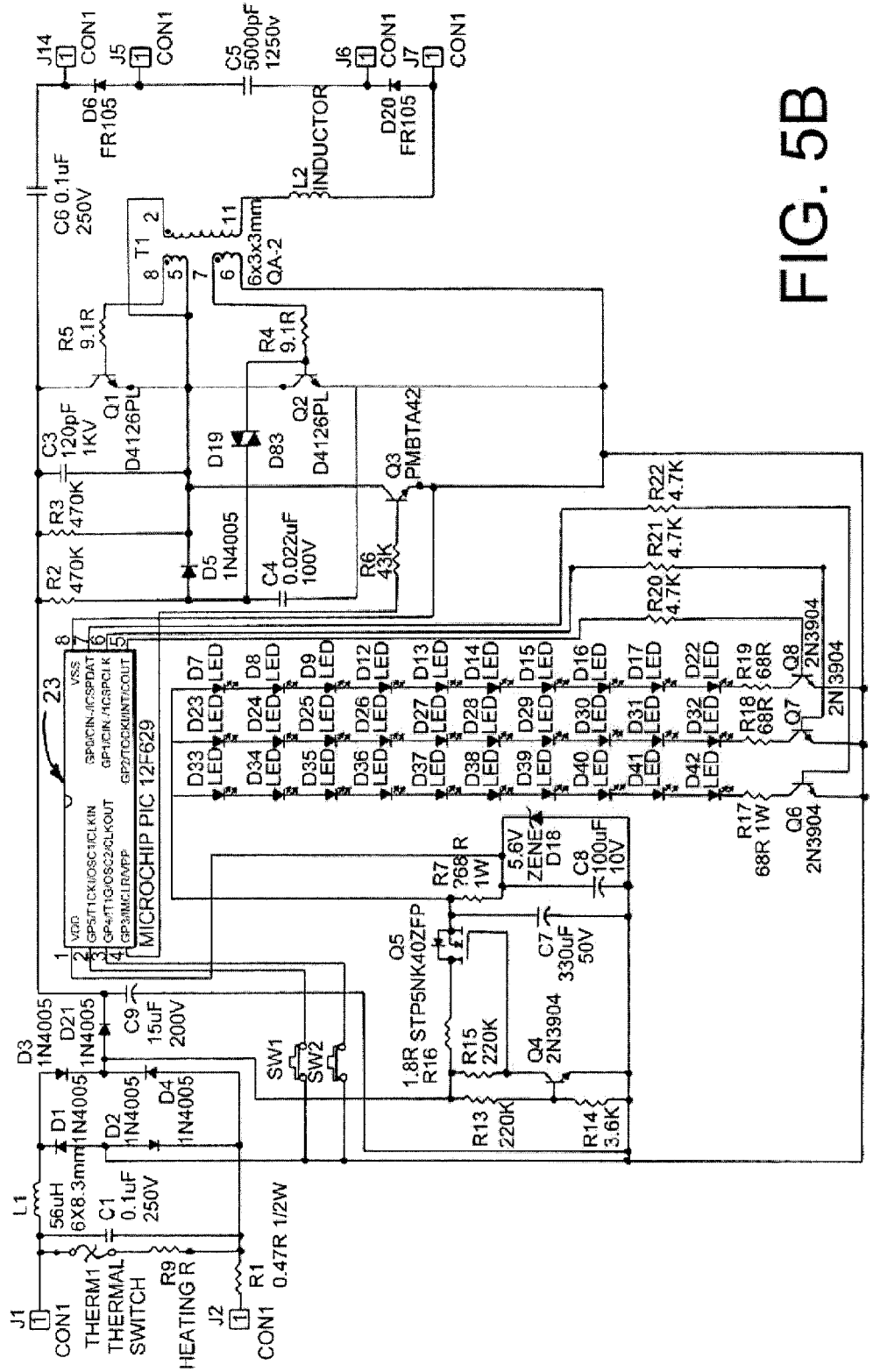
FIG. 5B is another circuit diagram illustrating another main control board suitable for the devices shown in FIGS. 1-4.
Figure 5C:
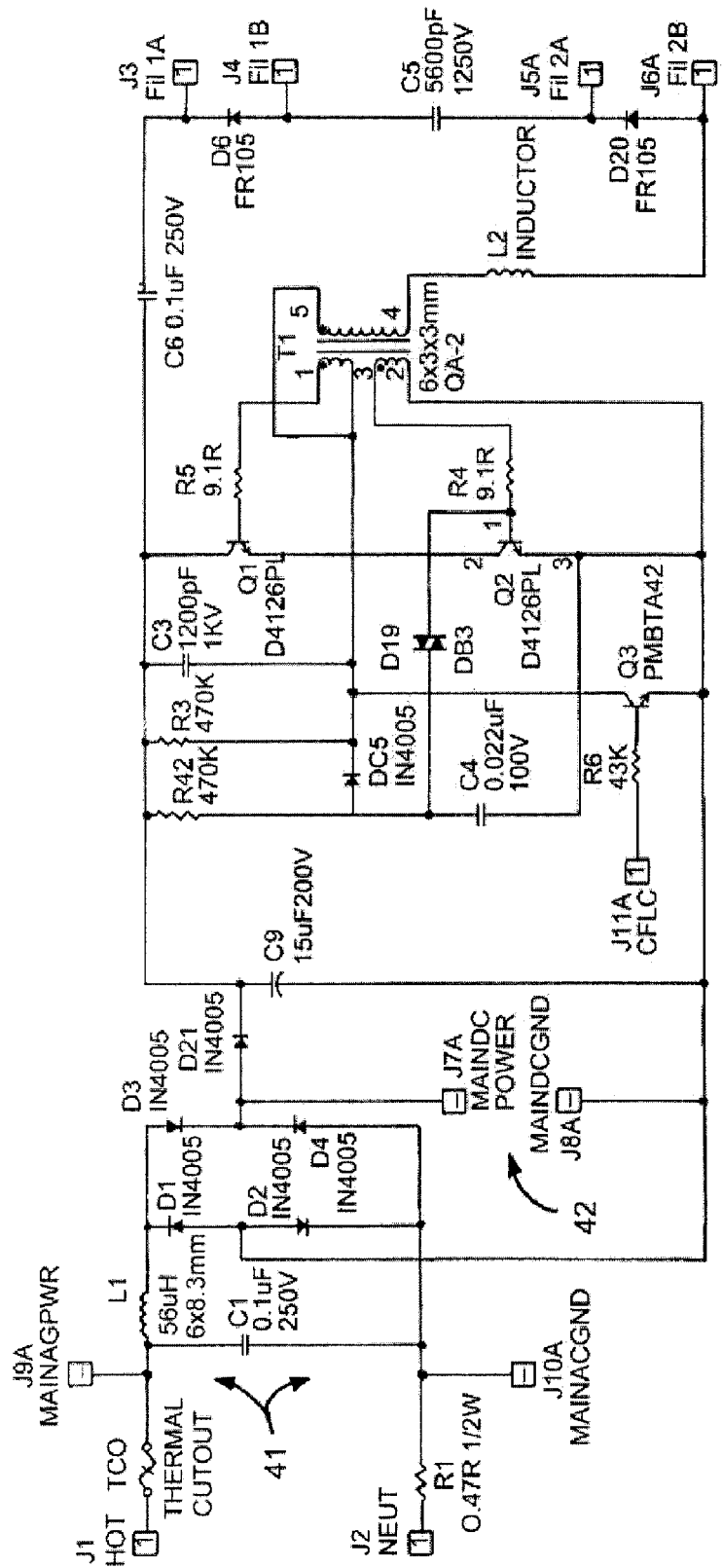
FIG. 5C is another circuit diagram illustrating a control board that is coupled to the control board illustrated in FIG. 5B.

FIG. 5A shows a circuit diagram for control arrangements for operating devices 10a-10c that produce a coordinated/combined presentation of light and volatile active. A microcontroller (or ASIC) 23 controls the operation of the device 10 As seen in FIGS. 5B and 5C, the controller 23 may be a PIC 12F629, which is an 8-pin flash-based 8-Bit CMOS microcontroller with a +/−1% internal 4 MHz oscillator The operating voltage range is from 2 to 5.5 V with an operating current of 100 µA at 1 MHz and 2 V The typical operating current with internal 4 MHz oscillator at 5 V is a few µA. It is possible that the controller 23 drive up to 25 mA to ground or Vcc on every I/O pin. The usable temperature range is from −40° C. to +125° C., which makes it suitable for outdoor use. The controller chips 23 have 1024 words of programmable flash memory, 128 bytes of EEPROM and 64 bytes of RAM.

Returning to FIG. 5A, power is supplied to the devices 10a-10c through a lamp (AC power source 41). A voltage conversion device 42 converts the AC voltage from the AC power source 41 to a DC voltage The microprocessor 23 receives power from voltage conversion device 42 and controls the operation of device 10 using the received power.

Microcontroller 23 includes a control logic 43 that provides the operational instructions to the various elements of the device 10 in accordance with input signals or internal programs The control logic 43 converts received signals or runs internal software routines to set the operation of the allay of LEDs 15a-c and/or the volatile active control system D with a resistor R1 acting as the heater In an embodiment using a fan 31 instead of a heater 28, R1 would be replaced by motor 32.

The control logic 43 sends a signal for controlling the operation of the array of LEDs to LED control block 44 When using pulse width modulation to drive and control the LED array, the LED control block 44 sets the duty cycles for the LEDs based on the instruction from the control logic 43.

Supply lines 45a-45c supply voltage across resistors 46a-46c, from power supply 42 Preferably, the voltage supplied across resistors 46a-46c is between about 3.5 and about 5.0 volts Resistors 46a-46c in turn power a red LED 15a, a green LED 15b, and a blue LED 15c, respectively Field effect transistors (FEIs) 47a-47c are turned on and off in accordance with the respective duty cycles generated by the LED control block 44. Operation of the FETs 47a-47c control the RGB LEDs 15a-15c to be activated for the portions of the duty cycle set by the LED control block 44. Thus, the intensity and color of the light emitted from the LEDs 15a-15c can be varied to produce the desired effects. Typically, pulse width modulation is used to control a constant current to be applied to a given diode for a set period of one duty cycle, thus controlling the total current applied to the LED over the full duty cycle. Thus, the diode flickers on for the set portion of each duty cycle, and off for the remainder of the duty cycle. Of course, this on and off operation is so fast (a typical duty cycle is in the range of a few milliseconds) that the intensity of the diode appears constant to an observer (with no discernable flicker), until the set period of activation over the duty cycle is changed.

The microprocessor 23 may also send a control signal to volatile active control D, as shown in FIG. 5A. In this embodiment, the volatile active dispenser being controlled is an evaporative-type dispenser A resistor R1 that is part of the heating element 28 is heated by a current passing across the resistor R1. Typically, the resistor R1 is placed adjacent to an area at which a volatile active-containing gel or oil is exposed to air and the heat from the resistor R1 causes the volatile active to be vaporized. A switch SCR1 varies the current passing across the resistor R1, thus varying the heat produced by resistor R1 and the rate of vaporization of the volatile active. In alternative embodiments, the resistor R1 may be replaced and/or supplemented by a fan which is controlled by switch SCR1, or an atomization device. Also, switch SCR1 may be replaced by an FET in other embodiments. Further, the volatile active dispenser may also be mechanically adjusted by a user, rather than through a microprocessor.

Microprocessor 23 may also control a use-up cue 25. The use-up cue 25 may track the use of volatile active control to estimate the time at which the volatile active in the volatile active dispenser is likely to be used up or may simply employ a sensor to detect when a cartridge, bottle, tube or other active device is empty or depleted. When the use-up cue 25 determines that volatile active has been spent, in one embodiment, it sends a signal to LED control block 44 to cause the LEDs to illuminate in a pattern, color, or other manner to indicate to a user that it is time to replace the volatile active in the dispenser if a refillable dispenser is used, or more preferably, the volatile active cartridges 17 or 18. A large variety of cartridge-type containers, mats, bottles or inserts may be utilized for the "cartridges" 17, 18 disclosed herein. Various other designs embodiments will be apparent to those skilled in the art. Further, suitable means for determining or communicating to the use-up cue 25 when a particular cartridge 17, 18 is empty, near-empty or exhausted will also be apparent to those skilled in the art A simple resistance mechanism may be desirable due to low-cost and dependability.

Figure 5D:
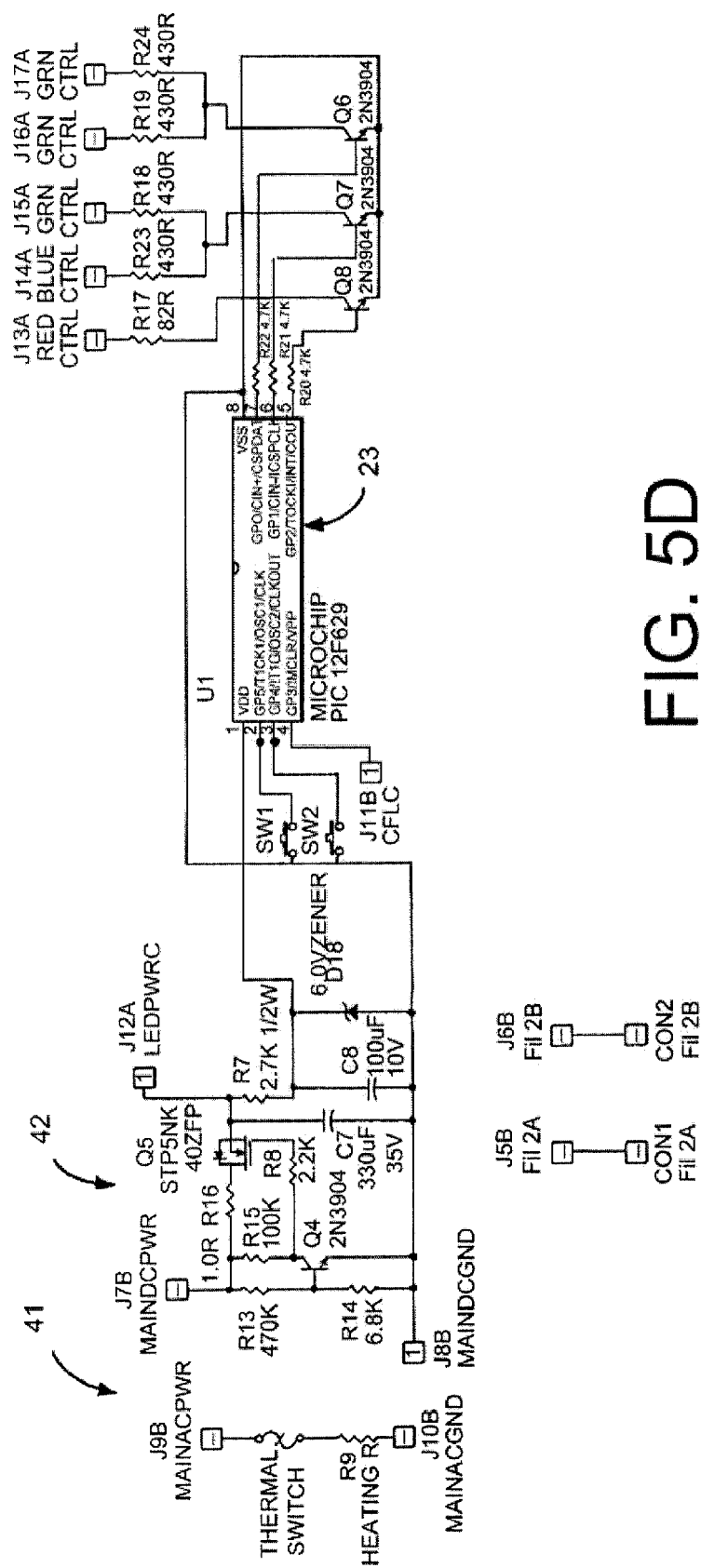
FIG. 5D is another circuit diagram illustrating a control board that is coupled to the control board illustrated in FIG. 5B.
Figure 5E:
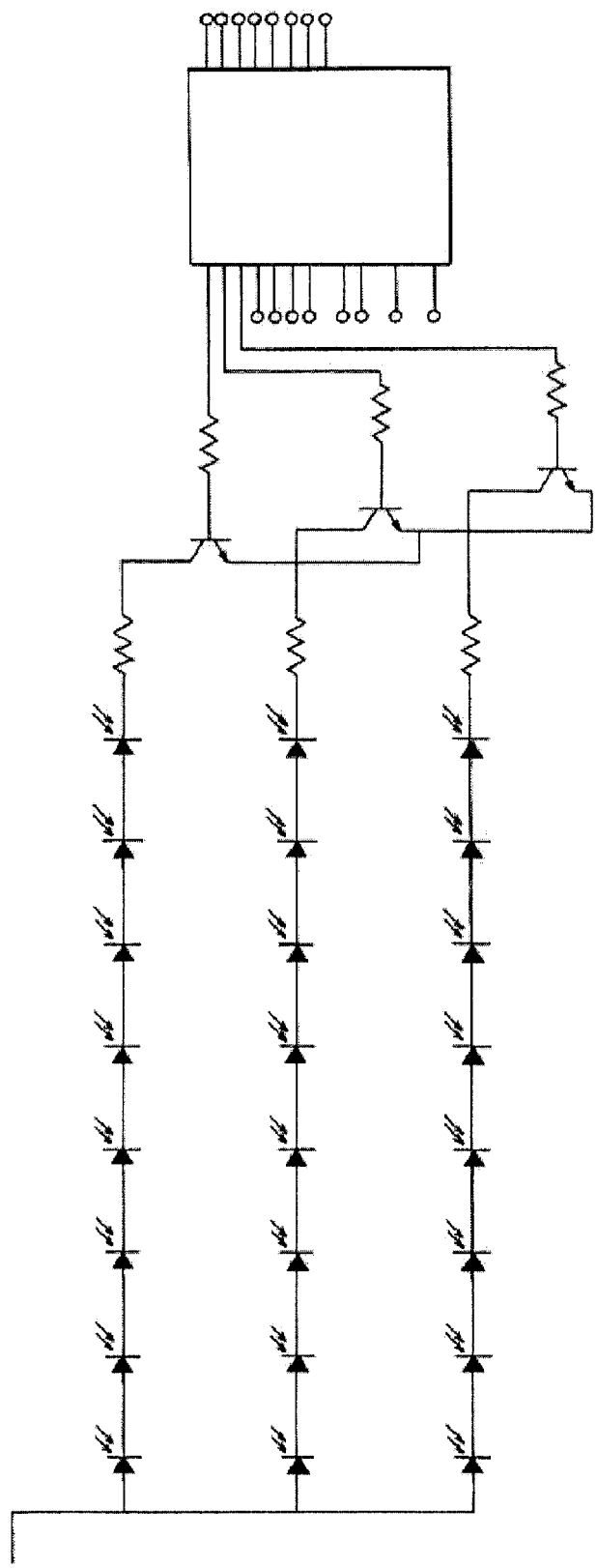
FIG. 5E is a circuit diagram for the LED drivers for the devices shown in FIGS. 1-3.

The control logic 43 may be programmed/controlled in any number of ways. In one embodiment, useful for outdoor or indoor light-systems comprising a plurality of devices 10, the network card 27 receives an external signal, through an antenna 48. For single device systems, the card 27 functions as a transceiver for receiving signals through the antenna 48 from a remote control (not shown). The received signal is transmitted from the network card 27 to control logic 43 to set the presentation of light through the LED control block 44 and the volatile active control dispenser D. Also, the operation of the control logic 43 may be set by an internal program. Variations of the above circuitry are illustrated in FIGS. 5B-5D

A user may manually set the volatile active output rate and light show. In this case, a program select switch 36 or 37 (FIGS. 1-2) may be operated by a user to set a light show program for the LEDs 15a-15c. One of the switches 36, 37 may also be used to control rate of release of the insect control material. Of course, additional buttons or switches may be provided, depending on the level of the control and programmability desired. In particular, a switch can be provided to control whether manual or automatic operation/programming is desired.

The intensity and exact color of the light emitted from the housing of the device 10 may be varied by changing the current applied to each diode The different combinations of LED operations will alter the perceived color when the light from the LEDs is diffused to form one perceived color. This is best understood in connection with FIG. 6 which shows a CIE chart with three coordinates corresponding to three different-colored (RGB) LEDs. The light show as described herein includes starting and ending color points and proceeding along any predefined path between those two points during the course of a show. This is explained in greater detail in pending Provisional Application No. 60/641,441, which is also incorporated herein by reference.

A color point refers to the settings of the LEDs at a given moment of the light show, which provides a specific perceived color. (As the settings of the LEDs change over time in accordance with the instructions for the light show, the color points can ultimately be perceived as a "wash" or "waves" of colors.) Because we are discussing "perceived" colors, the starting color point does not directly correspond to the wavelengths of light emitted by the LEDs used in the color show, inasmuch as those wavelengths are substantially constants The starting and ending color points can, however, be defined by coordinates on the CIE chart.

The color points can also be defined by the relative intensities of the lights emitted from the LEDs used to produce the color show (i.e, the operational settings for the different LEDs at specified points of the light show). For instance, a color point can be defined by the specific intensity level set at that point in time for each LED being used, and the dominant wavelength of each LED. Preferably, intensity levels will be defined by the pulse widths of the LEDs (e.g., as a percentage of full intensity of the LEDs)

It will be understood by one of ordinary skill in the art that the combination of the lights from different-colored LEDs at specified intensities will directly correspond to a set point on the CIE chart. Therefore, the different possible methods discussed above for defining the color points (i.e., using CIE chart coordinates of specific LED settings) are substantially equivalent for purposes of defining a perceived color.

We note, however, that there are many ways in which the lights from the different LEDs can be combined. In some methods, especially where diffusers are not used and the LEDs are merely placed in close proximity to each other, a user may perceive different colors close to the emission points of the LEDs. When we discuss color points, we refer to the color of a substantially complete mixture of the lights from the different LEDs, even though there may be observable portions of the display in which the user sees distinct colors corresponding to the wavelengths from the individual LEDs, rather than the complete mixture.

The starting and ending color points are similar to the first and last entries in a look-up table setting forth all of the points of a color show in a conventional system; however, instead of providing all of the intervening points from the conventional look-up table, our invention can dispense with the need to determine and store each and every intervening color point. To achieve this effect, timing information is provided. The timing information defines timing aspects of the light show and LED control Using the timing information, a microcontroller may calculate all of the intervening color points for the light show on its own This saves valuable memory space that would otherwise have to be devoted to complex look-up tables for various light shows. The timing information preferably includes information concerning the duration of the show, from display of the starting color point to the ending color point. The timing information also preferably includes information concerning the ramp speed for the LEDs, either as a whole, or individually. The ramp speed refers to the speed of intensity change of the LEDs. Generally, lamp speed may be defined as the unit of time it takes the LED to change one intensity level (for that particular show), with each intensity level being equal This can also be defined as the change of intensity per unit of time.

The LEDs may be controlled by pulse width modulation (PWM) such that the pulse width of a constant current applied for a portion of the duty cycle is varied to alter the intensity of the light emitted from the LED. The intensity level of the LED can be measured as a fraction of the duty cycle during which the constant current is applied, which, among other ways, can be expressed as a percentage When an LED is not on, the pulse width is at 0%. When a constant current is applied to the LED for half of the duty cycle, the intensity of the LED is at 50%. Ramp speed maybe defined as the amount of time between changes of intensity of one percentage point of total intensity. Consequently, if the lamp speed of an LED is set at two seconds, then during the course of the light show that LED will change its intensity by one percentage point every two seconds until teaching the target value (i e., the intensity value of the LED for achieving the ending color point). In an embodiment, lamp speed is defined as the percentage change per second. Of course, the speed can be defined in any one of a number of ways, as would be understood by one of ordinary skill in the art. Also, the tamp speed can be a positive or negative value, depending on whether the intensity of the LED is to be increased or decreased during the light show. Alternatively, the microcontroller 23 can be programmed to increase or decrease the intensity setting by comparing the starting intensity setting to the ending intensity setting. Thus, for instance, if the microcontroller 23 determines that the value of the ending setting is lower than the value of the starting setting, the microcontroller 23 will decrease the intensity of the LED at a rate set by the given ramp speed.

Figure 6:
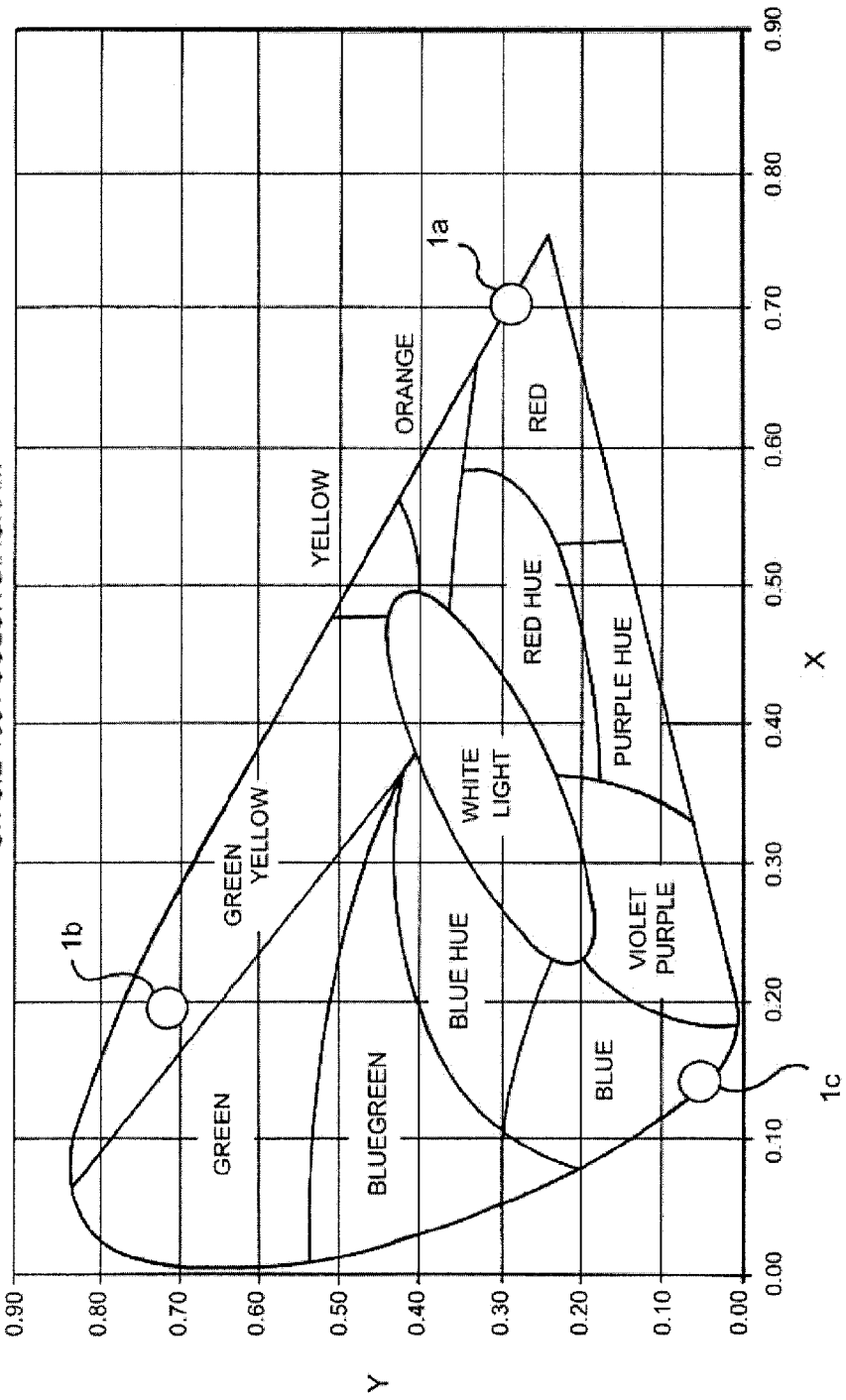
FIG. 6 shows an exemplary CIE chart with three coordinates corresponding to three LEDs of different colors, red, green and blue, wherein a light show presented in accordance with this disclosure comprises any path disposed within the boundaries of the curve carried out over time.

With the timing information provided, the microcontroller 23 controlling the LEDs 15a-15c can be provided with logic that calculates the intervening color points between the starting and ending points of the CIE chart of FIG. 6. The logic reads the timing information from memory and adjusts the duty cycle for each LED in accordance with the ramp speed and target intensity. The intensity for each LED is adjusted until the target value is reached or the duration of the show has been reached. At this time, the microcontroller 23 will read the next set of timing information from memory and begin again. Of course, if the target intensity is reached prior to the duration of the show, the microcontroller 23 will hold the intensity of the LED until the duration is reached. If a continuously changing show is desired, the ramp speed may be set such that the target intensity is not reached prior to the duration of the show and thus, the target value will never be reached. Likewise, the microcontroller may be configured to ignore the duration, and load the next intensity and ramp speed as soon as the target intensity is reached.

The programming for achieving this would be readily understood by one of ordinary skill in the art Accordingly, a detailed description of the many different ways of programming the microcontroller will not be provided her and While three colored LEDs 15a, 15b, 15c are shown with respect to the device 10b in FIG. 2 and six colored LEDs 15a', 15b', 15c' are shown with respect to the device 10c in FIG. 3, any number of LEDs or RGB LED clusters may be used. In addition, the choice of which color LEDs to provide may be dictated by design preferences. Further, the use of LEDs is not necessary as incandescent or conventional colored light sources may be employed using the same techniques as described above Generally, one of each colored light will be provided in close proximity to the other colored lights. With such a cluster arrangement, the exact color of each light of the set of three different colors can be adjusted to create a blended color, for example, amber or purple. This blending can be achieved by providing the three lights in such close proximity that the observer only sees the blend of colored lights, rather than each individual colored light. Alternatively, or in addition, a diffuser may be provided to diffuse the light of the three lights to produce the combined color. In other embodiments, the lights may be projected off of a surface to be combined before being viewed by an observer. When the LEDs are not placed close to each other, or there is not sufficient diffusion, multiple colors may be perceived in the device 10. This is a matter of design preference.

LEDs and incandescent light sources are readily available from lighting manufactures in a wide variety of colors. Also, the arrangement and operation of LEDs or other types of colored light sources to achieve a desired presentation will be apparent to one of ordinary skill in the art.

Figure 8:
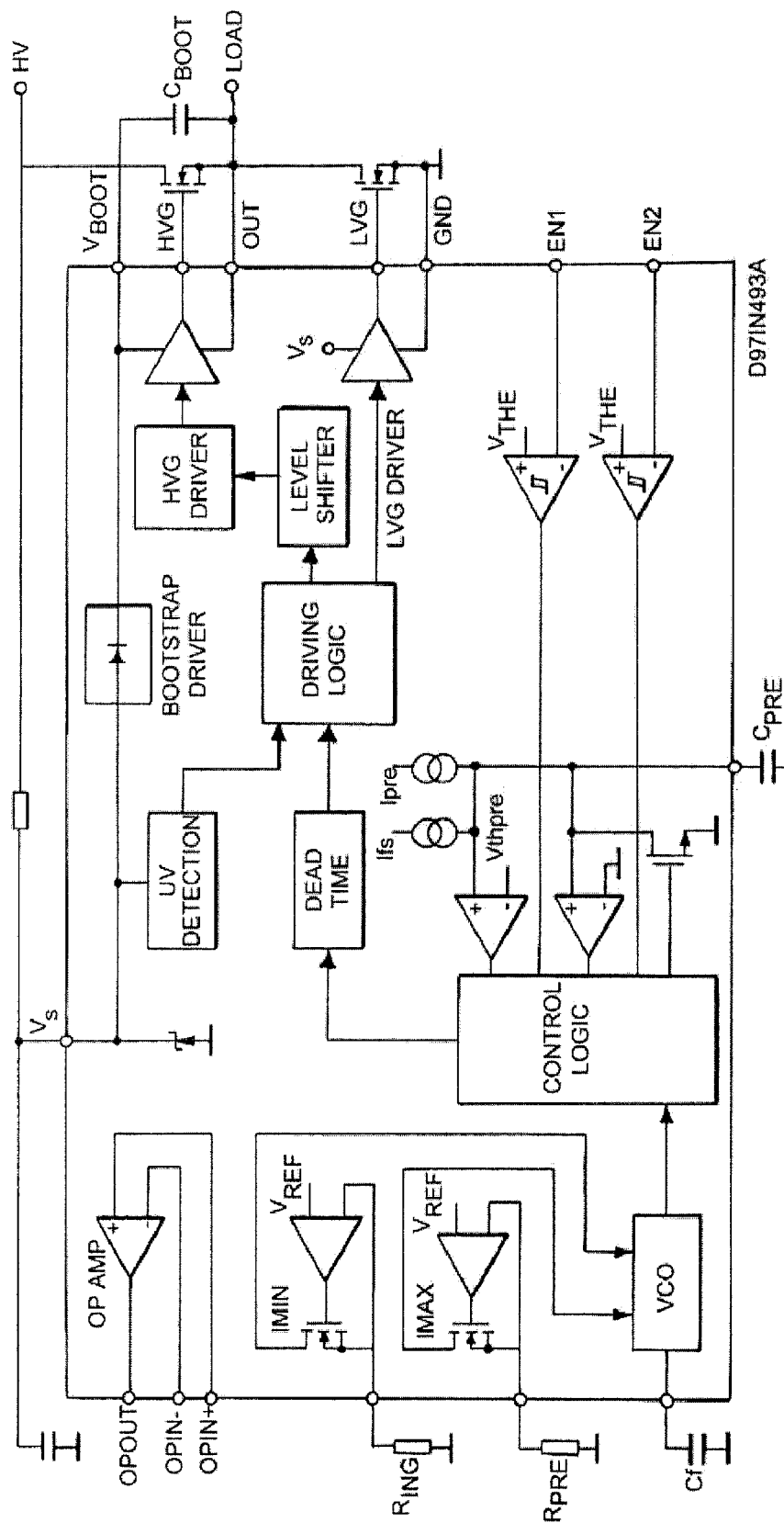
FIG. 8 is a circuit diagram for the microprocessor of the dimmable ballast for the coiled fluorescent lamp (CFL) shown in FIG. 7.
Figure 9:
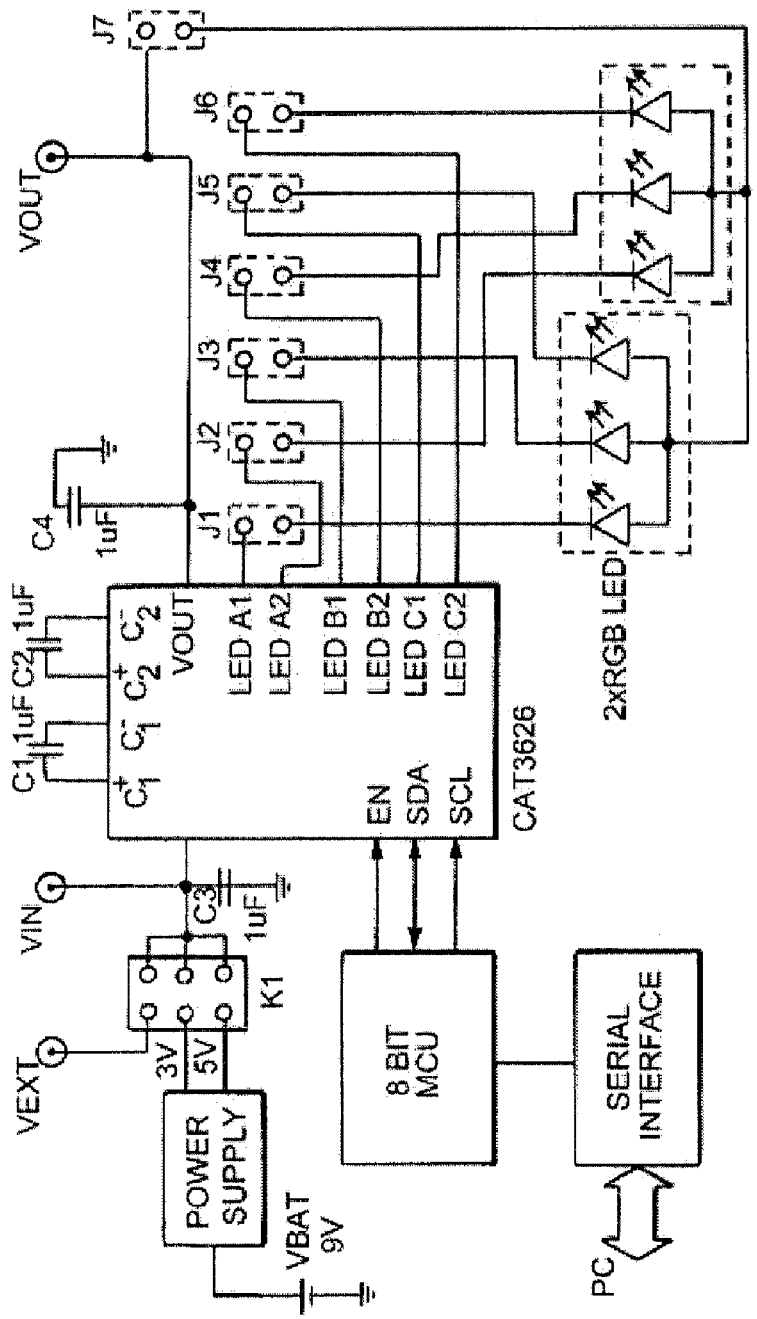
FIG. 9 is a circuit diagram for an exemplary LED driver for the devices shown in FIGS. 2-3
Figure 10:
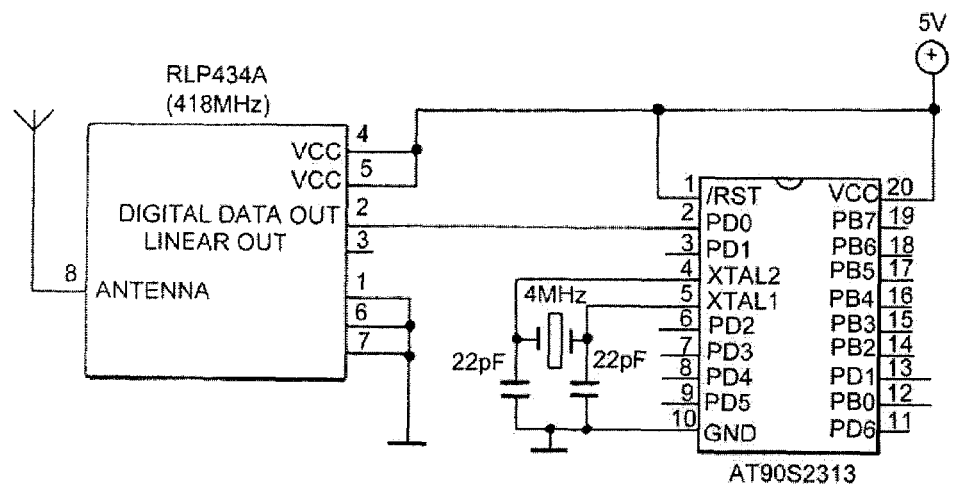
FIG. 10 is a circuit diagram for the radiofrequency (RF) receiver for the devices shown herein employing a remote control
Figure 11:
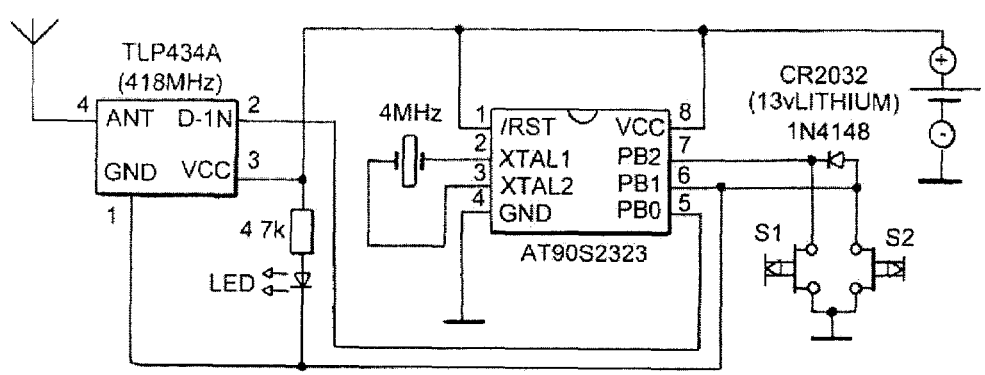
FIG. 11 is a circuit diagram of for the RF transmitter for the devices shown herein employing a remote control.

A circuit diagram for a dimming ballast 22 for a CFL is shown in FIG. 7. Of course, other ballast designs will work and will be apparent to those skilled in the art. FIG. 8 shows a circuit diagram for the L6574 processors shown in FIG. 7. The L6574, as shown in FIG. 8, is available from ST Microelectronics (www st com), includes a dedicated timing section enabling the parameters for proper pre-heat and ignition of a CFL 14 to be set Further, the L5674 also includes the OP AMP (FIG. 8) for implementing closed loop control of the lamp current during operation thereby enabling the user to dim the CFL 14 Returning to FIG. 7, the pin connections for the L5674 are as follows: (1) preheat timing capacitor; (2) maximum oscillation frequency setting; (3) are so later frequency setting capacitor; (4) minimum oscillation frequency setting resistor; (5) operational amplifier for purposes of implementing a feedback control loop; (6) converting the input of the operational amplifier; (7) non-inverting the input of the operational amplifier; (8) enable 1 which forces the device in a latched shut down state under predetermined voltage conditions; (9) enable 2 which restarts the start-up procedure; (10) ground; (11) low side driver output; (12) supply voltage; (13) not connected; (14) high side driver floating reference; (15) high side drive output; and (16) bootstrapped supply voltage An exemplary LED drivel circuit is shown in FIG. 9 that is available from catalyst semiconductor, Inc. Other examples may be found in U.S. Pat. Nos. 6,150,774 and 6,528,924, which are incorporated herein by reference. The driver circuit shown in FIG. 9 is controlled by the microcontroller 23. For those embodiments employing a remote control, a suitable RF receiver circuit diagram is shown in FIG. 10 and a suitable RF transmitter circuit diagram is shown in FIG. 11

Turning to FIG. 12, an outdoor light system 50 is disclosed which includes a plurality of the combination light/active release devices 10 disclosed herein that surround an area 51 to be protected, such as a porch or patio and, or in the alternative, such light/active release devices can be used to protect a pathway shown at 52. The devices 10 may be powered by an electrical currant, or as discussed above, may be solar powered. Communication between the devices may be hardwired or wireless communication may be employed Timers may be especially useful in these types of systems as the release of the insect controlled material or mosquito repellant maybe delay until dusk, increased at dusk or otherwise adjusted during various times depending upon when the pests at issue are problematic.

Figure 13:
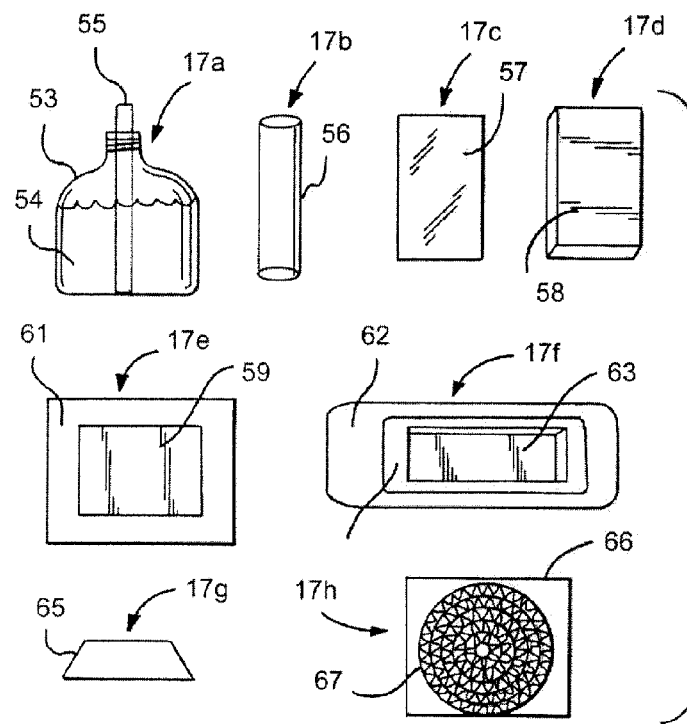
FIG. 13 illustrates various form of active ingredient cartridges, mats, tubes, bottles, sheets, substrates and other impregnated structures.

Finally, turning to FIG. 13, various embodiments of the replaceable inserts 17 are illustrated. The insert 17a includes a bottle 53 filled with insect control material 54 and a wick 55. The replaceable insert 17b includes a tubular structure 56 which may be permeable in nature for controlled release. The replaceable insert 17c includes a single sheet 57 that maybe transparent, translucent or opaque. One or more of these sheets 57 maybe inserted into the slot 16. The insert 17d includes a thicker mat 58 impregnated with the active material. The insert 17e would be used in a embodiment without a slot 16 and would be affixed to an exterior of the base 12 of the device 10. A central patch 59 is impregnated with active material and the outer boundary 61 is used to adhere the replaceable patch 17e to the device 10 The insert 17f includes an outer flame 62, preferably made from plastic or foil and an inner trouth or tray area 63 that accommodates the active material. A permeable membrane 64 is used to cover the troth 63 for controlled release of the active The insert 17g is a compressed sand or sand core tablet 65 impregnated with active material. This technology is described WO 2004/068945 incorporated herein by reference. Finally, the insert 17h includes an outer flame 66 that accommodates a honeycomb structure 67 which is essentially a round, flat, cardboard disc impregnated with active material The space in between the corrugated elements provides sufficient airflow and controlled release of the active impregnated into the honeycomb structure 67. Of course, other types of inserts will be apparent to the skilled in the art and are considered to fall within the scope of the disclosure.

These figures show only some possible arrangements for configuring, controlling and programming the disclosed devices. Many different embodiments may be constructed without departing from the spirit and scope of this disclosure. It should be understood that disclosure is not limited to the specific embodiments described in this specification To the contrary, this disclosure is intended to cover various modifications and equivalent arrangements included within the spirit and scope of this disclosure as defined by the claims. The scope of the claims is to be accorded the broadest interpretation so as to encompass all such modifications, equivalent structures and functions.

INDUSTRIAL APPLICABILITY

The devices of this disclosure makes it possible to achieve an overall desired effect by providing active ingredient emission including insect control, mood lighting and functional white lighting from a single device that resembles a conventional light bulb.

What is claimed:

1. A combination light and volatile active dispenser device, comprising:
   a translucent housing comprising an open bottom;
   the open bottom of the housing being connected to a base;
   the base being connected to a connector for mating with a light socket, the base being disposed between the translucent housing and the connector;
   the base being coupled to a light source, the base accommodating a replaceable insert comprising an insect control material.

2. The device of claim 1 wherein the light source comprises a coiled fluorescent light (CFL).

3. The device of claim 2 wherein the light source comprises a plurality of colored lights and the device further comprises a control circuitry comprising a memory with at least one colored light show stored in the memory.

4. The device of claim 3 wherein the control circuitry comprises a dimmable electronic ballast for adjusting an intensity level of the CFL.

5. The device of claim 1 wherein the light source comprises a plurality of colored lights and the device further comprises a control circuitry comprising a memory with at least one colored light show stored in the memory.

6. The device of claim 1 wherein the insect control material comprises at least one material selected from the group consisting of:
   (3-phenoxyphenyl)methyl 3-(2,2-dichloroethenyl)-2,2-dimethylcyclopropanecarboxylate;
   (2-methyl[1,1'-biphenyl]-3-yl)methyl 3-(2-chloro-3,3,3-trifluoro-1-propenyl)-2,2-dimethylcyclopropanecarboxylate;
   (S)-2-methyl-4-oxo-3-(2-propynyl)-2-cyclopenten-1-yl 2,2-dimethyl-3-(2-methyl-1-propenyl)cyclopropanecarboxylate;
   d-allethrin-2-methyl-4-oxo-3-(2-propynyl)-2-cyclopenten-1-yl 2,2-dimethyl-3-(2-methyl-1-propenyl)cyclopropanecarboxylate;
   [1R-[1a(S*),3b]]-2-methyl-4-oxo-3-(2-propenyl)-2-cyclopenten-1-yl 2,2-dimethyl-3-(2-methyl-1-propenyl)cyclopropanecarboxylate;
   (1,3,4,5,6,7-hexahydro-1,3-dioxo-2H-isoindol-2-yl)methyl 2,2-dimethyl-3-(2-methyl-1-propenyl)cyclopropanecarboxylate;
   (1,3,4,5,6,7-hexahydro-1,3-dioxo-2H-isoindol-2-yl)methyl (1R)-cis-trans-2,2-dimethyl-3-(2-methyl-1-propenyl)cyclopropanecarboxylate and mixed stereoisomers;
   (3-phenoxyphenyl)methyl 2,2-dimethyl-3-(2-methyl-1-propenyl)cyclopropanecarboxylate and mixed stereoisomers;
   [2,3,5,6-tetrafluoro-4-(methoxymethyl)phenyl]methyl 2,2-dimethyl-3-(1-propenyl)cyclopropanecarboxylate;
   (2,3,5,6-tetrafluoro-4-methylphenyl)methyl 2,2-dimethyl-3-(1-propenyl)cyclopropanecarboxylate;
   [2,3,5,6-tetrafluoro-4-(methoxymethyl)phenyl]methyl 2,2-dimethyl-3-(2-methyl-1-propenyl)cyclopropanecarboxylate;
   (1R-trans)-(2,3,5,6-tetrafluorophenyl)methyl 3-(2,2-dichloroethenyl)-2,2-dimethylcyclopropanecarboxylate;
   [2,5-dioxo-3-(2-propynyl)-1-imidazolidinyl]methyl 2,2-dimethyl-3-(2-methyl-1-propenyl)cyclopropanecarboxylate;
   1-ethynyl-2-methyl-2-pentenyl(1R)-cis-trans-2,2-dimethyl-3-(2-methyl-1-propenyl)cyclopropanecarboxylate;
   2,2-dichioroethenyl dimethyl phosphate;
   [1 a,3a(Z)]-(±)-(2,3,5,6-tetrafluoro-4-methylphenyl)methyl 3-(2-chloro-3,3,3-trifluoro-1-propenyl)-2,2-dimethylcyclopropanecarboxylate;
   ((R)-trans isomers)-(3-phenoxyphenyl)methyl 2,2-dimethyl-3-(2-methyl-1-propenyl)cyclopropanecarboxylate;
   cyano(3-phenoxyphenyl)methyl 3-(2,2-dichloroethenyl)-2,2-dimethylcyclopropanecarboxylate;
   1-[[2-(4-ethoxyphenyl)-2-methylpropoxy]methyl]-3-phenoxybenzene;
   1-methylpropyl2-(2-hydroxyethyl)-1-piperidinecarboxylate;
   N,N-diethyl-m-toluamide-N,N-diethyl-3-methylbenzamide; and mixtures thereof.

7. The device of claim 1 wherein the replaceable insert comprises a cartridge and the base comprises a slot for receiving the cartridge, the cartridge containing the insect control material.

8. The device of claim 1 wherein the replaceable insert comprises a mat impregnated with the insect control material and the base comprises a slot for receiving the mat.

9. The device of claim 1 wherein the base comprises at least one vent for releasing the insect control material.

10. The device of claim 1 further comprising at least one of a fan or piezoelectric atomizer disposed within the base and directed at the insert and the base comprises at least one vent for releasing the insect control material.

11. The device of claim 1 further comprising a heating element disposed within the base for volatilizing the insect control material of the insert and the base comprises at least one vent for releasing the insect control material.

12. The device of claim 1 wherein the light source comprises a low voltage white light source.

13. A combination light and insect control material dispensing device, comprising:
    a translucent housing comprising an open bottom;
    the open bottom of the housing connected to a base;
    the base disposed between and connected to the translucent housing and a connector for engaging a light socket,
    the base accommodating a replaceable insert comprising an insect control material, and the base comprising a vent for releasing the insect control material,
    the base further accommodating a fan directed at the insert and vent.

14. The device of claim 13 wherein the light source comprises a coiled fluorescent light (CFL).

15. The device of claim 13 wherein the light source comprises a plurality of colored LEDs and the device further comprises a control circuitry comprising a memory with at least one colored light show stored in the memory.

16. The device of claim 13 wherein the insect control material comprises at least one material selected from the group consisting of:
    (3-phenoxyphenyl)methyl 3-(2,2-dichloroethenyl)-2,2-dimethylcyclopropanecarboxylate;
    (2-methyl[1,1'-biphenyl]-3-yl)methyl 3-(2-chloro-3,3,3-trifluoro-1-propenyl)-2,2-dimethylcyclopropanecarboxylate;
    (S)-2-methyl-4-oxo-3-(2-propynyl)-2-cyclopenten-1-yl 2,2-dimethyl-3-(2-methyl-1-propenyl)cyclopropanecarboxylate;
    d-allethrin-2-methyl-4-oxo-3-(2-propenyl)-2-cyclopenten-1-yl 2,2-dimethyl-3-(2-methyl-1-propenyl)cyclopropanecarboxylate;
    [1R-[1a(S*),3b]]-2-methyl-4-oxo-3-(2-propenyl)-2-cyclopenten-1-yl 2,2-dimethyl-3-(2-methyl-1-propenyl)cyclopropanecarboxylate;
    (1,3,4,5,6,7-hexahydro-1,3-dioxo-2H-isoindol-2-yl)methyl 2,2-dimethyl-3-(2-methyl-1-propenyl)cyclopropanecarboxylate;
    (1,3,4,5,6,7-hexahydro-1,3-dioxo-2H-isoindol-2-yl)methyl (1R)-cis-trans-2,2-dimethyl-3-(2-methyl-1-propenyl)cyclopropanecarboxylate and mixed stereoisomers;
    (3-phenoxyphenyl)methyl 2,2-dimethyl-3-(2-methyl-1-propenyl)cyclopropanecarboxylate and mixed stereoisomers;
    [2,3,5,6-tetrafluoro-4-(methoxymethyl)phenyl]methyl 2,2-dimethyl-3-(1-propenyl)cyclopropanecarboxylate;
    (2,3,5,6-tetrafluoro-4-methylphenyl)methyl 2,2-dimethyl-3-(1-propenyl)cyclopropanecarboxylate;
    [2,3,5,6-tetrafluoro-4-(methoxymethyl)phenyl]methyl 2,2-dimethyl-3-(2-methyl-1-propenyl)cyclopropanecarboxylate;
    (1R-trans)-(2,3,5,6-tetrafluorophenyl)methyl 3-(2,2-dichloroethenyl)-2,2-dimethylcyclopropanecarboxylate;
    [2,5-dioxo-3-(2-propynyl)-1-imidazolidinyl]methyl 2,2-dimethyl-3-(2-methyl-1-propenyl)cyclopropanecarboxylate;
    1-ethynyl-2-methyl-2-pentenyl (1R)-cis-trans-2,2-dimethyl-3-(2-methyl-1-propenyl)cyclopropanecarboxylate;
    2,2-dichloroethenyl dimethyl phosphate;
    [1 a,3a(Z)]-(±)-(2,3,5,6-tetrafluoro-4-methylphenyl)methyl 3-(2-chloro-3,3,3-trifluoro-1-propenyl)-2,2-dimethylcyclopropanecarboxylate;
    ((R)-trans isomers)-(3-phenoxyphenyl)methyl 2,2-dimethyl-3-(2-methyl-1-propenyl)cyclopropanecarboxylate;
    cyano(3-phenoxyphenyl)methyl 3-(2,2-dichloroethenyl)-2,2-dimethylcyclopropanecarboxylate;
    1-[[2-(4-ethoxyphenyl)-2-methylpropoxy]methyl]-3-phenoxybenzene;
    1-methylpropyl 2-(2-hydroxyethyl)-1-piperidinecarboxylate;
    N,N-diethyl-m-toluamide-N,N-diethyl-3-methylbenzamide; and mixtures thereof.

17. A combination light and insect control material dispensing device, comprising:
    a translucent housing comprising an open bottom;
    the open bottom of the housing being connected to a base;
    the base disposed between and connected to a translucent housing and a connector for engaging a light socket,
    the base accommodating a replaceable insert comprising an insect control material, and a vent for releasing the insect control material,
    the base further accommodating a heating element for volatilizing the insect control material.

18. The device of claim 17 wherein the light source comprises a coiled fluorescent light (CFL).

19. The device of claim 17 wherein the light source comprises a plurality of colored LEDs and the device further comprises a control circuitry comprising a memory with at least one colored light show stored in the memory.

20. The device of claim 17 wherein the insect control material comprises at least one material selected from the group consisting of:
    (3-phenoxyphenyl)methyl 3-(2,2-dichloroethenyl)-2,2-dimethylcyclopropanecarboxylate;
    (2-methyl[1,1'-biphenyl]-3-yl)methyl 3-(2-chloro-3,3,3-trifluoro-1-propenyl)-2,2-dimethylcyclopropanecarboxylate;
    (S)-2-methyl-4-oxo-3-(2-propynyl)-2-cyclopenten-1-yl 2,2-dimethyl-3-(2-methyl-1-propenyl)cyclopropanecarboxylate;
    d-allethrin-2-methyl-4-oxo-3-(2-propenyl)-2-cyclopenten-1-yl 2,2-dimethyl-3-(2-methyl-1-propenyl)cyclopropanecarboxylate;
    [1R-[1a(S*),3b]]-2-methyl-4-oxo-3-(2-propenyl)-2-cyclopenten-1-yl 2,2-dimethyl-3-(2-methyl-1-propenyl)cyclopropanecarboxylate;
    (1,3,4,5,6,7-hexahydro-1,3-dioxo-2H-isoindol-2-yl)methyl 2,2-dimethyl-3-(2-methyl-1-propenyl) cyclopropanecarboxylate;
    (1,3,4,5,6,7-hexahydro-1,3-dioxo-2H-isoindol-2-yl)methyl (1R)-cis-trans-2,2-dimethyl-3-(2-methyl-1-propenyl)cyclopropanecarboxylate and mixed stereoisomers;

(3-phenoxyphenyl)methyl 2,2-dimethyl-3-(2-methyl-1-propenyl)cyclopropanecarboxylate and mixed stereoisomers;

[2,3,5,6-tetrafluoro-4-(methoxymethyl)phenyl]methyl 2,2-dimethyl-3-(1-propenyl)cyclopropanecarboxylate;

(2,3,5,6-tetrafluoro-4-methylphenyl)methyl 2,2-dimethyl-3-(1-propenyl)cyclopropanecarboxylate;

[2,3,5,6-tetrafluoro-4-(methoxymethyl)phenyl]methyl 2,2-dimethyl-3-(2-methyl-1-propenyl)cyclopropanecarboxylate;

(1R-trans)-(2,3,5,6-tetrafluorophenyl)methyl 3-(2,2-dichloroethenyl)-2,2-dimethylcyclopropanecarboxylate;

[2,5-dioxo-3-(2-propynyl)-1-imidazolidinyl]methyl 2,2-dimethyl-3-(2-methyl-1-propenyl)cyclopropanecarboxylate;

1-ethynyl-2-methyl-2-pentenyl (1R)-cis-trans-2,2-dimethyl-3-(2-methyl-1-propenyl)cyclopropanecarboxylate;

2,2-dichloroethenyl dimethyl phosphate;

[1 a,3a(Z)]-(±)-(2,3,5,6-tetrafluoro-4-methylphenyl)methyl 3-(2-chloro-3,3,3-trifluoro-1-propenyl)-2,2-dimethylcyclopropanecarboxylate;

((R)-trans isomers)-(3-phenoxyphenyl)methyl 2,2-dimethyl-3-(2-methyl-1-propenyl)cyclopropanecarboxylate;

cyano(3-phenoxyphenyl)methyl 3-(2,2-dichloroethenyl)-2,2-dimethylcyclopropanecarboxylate;

1-[[2-(4-ethoxyphenyl)-2-methylpropoxy]methyl]-3-phenoxybenzene;

1-methylpropyl 2-(2-hydroxyethyl)-1-piperidinecarboxylate;

N,N-diethyl-m-toluamide-N,N-diethyl-3-methylbenzamide; and mixtures thereof.

\* \* \* \* \*

UNITED STATES PATENT AND TRADEMARK OFFICE
CERTIFICATE OF CORRECTION

PATENT NO. : 7,503,675 B2
APPLICATION NO. : 11/620966
DATED : March 17, 2009
INVENTOR(S) : Scott W. Demarest et al.

It is certified that error appears in the above-identified patent and that said Letters Patent is hereby corrected as shown below:

Column 16, Line 53: replace "dichioroethenyl" with --dichloroethenyl--

Column 17, Line 23: after "housing" add --being--

Column 18, Line 13: replace "dichioroethenyl" with --dichloroethenyl--

Column 20, Line 1: replace "dichioroethenyl" with --dichloroethenyl--

Signed and Sealed this

Sixteenth Day of June, 2009

JOHN DOLL
*Acting Director of the United States Patent and Trademark Office*